United States Patent
Moturu et al.

(10) Patent No.: US 10,740,438 B2
(45) Date of Patent: Aug. 11, 2020

(54) METHOD AND SYSTEM FOR CHARACTERIZING AND/OR TREATING POOR SLEEP BEHAVIOR

(71) Applicant: Ginger.io, Inc., San Francisco, CA (US)

(72) Inventors: Sai Moturu, San Francisco, CA (US); Karim Wahba, San Francisco, CA (US); Anmol Madan, San Francisco, CA (US)

(73) Assignee: Ginger.io, Inc., San Francisco, CA (US)

( * ) Notice: Subject to any disclaimer, the term of this patent is extended or adjusted under 35 U.S.C. 154(b) by 545 days.

(21) Appl. No.: 15/464,916

(22) Filed: Mar. 21, 2017

(65) Prior Publication Data
US 2017/0189641 A1 Jul. 6, 2017

Related U.S. Application Data

(63) Continuation-in-part of application No. 13/969,349, filed on Aug. 16, 2013, now Pat. No. 9,836,581.
(Continued)

(51) Int. Cl.
*G16H 50/50* (2018.01)
*G06F 19/00* (2018.01)
(Continued)

(52) U.S. Cl.
CPC ........ *G06F 19/3418* (2013.01); *A61B 5/0022* (2013.01); *A61B 5/4836* (2013.01);
(Continued)

(58) Field of Classification Search
None
See application file for complete search history.

(56) References Cited

U.S. PATENT DOCUMENTS 6,356,940 B1  3/2002 Short
7,188,151 B2  3/2007 Kumar et al.
(Continued)

FOREIGN PATENT DOCUMENTS

CN  101600008  12/2009
JP  2003339674  12/2003
(Continued)

OTHER PUBLICATIONS

"European Office Action application No. 13 829 654.6, dated Jun. 11, 2019."
(Continued)

*Primary Examiner* — Michael Tomaszewski
(74) *Attorney, Agent, or Firm* — Jeffrey Schox; Caitlin Ploch

(57) ABSTRACT

Embodiments of a method and system for improving sleep characterization and/or a sleeping-related disorder for a user associated with a sleep session can include receiving a log of use dataset corresponding to user digital communication behavior at a mobile device, the log of use dataset associated with the sleep session; receiving a supplementary dataset characterizing activity of the user and/or mobile device, the supplementary dataset associated with the sleep session; characterizing a sleep-related parameter for the user based on at least one of the log of use dataset and the supplementary dataset; determining a sleep care plan for the user based on the sleep-related parameter, the sleep care plan including a therapeutic intervention; and promoting a therapeutic intervention to the user according to the sleep care plan.

18 Claims, 10 Drawing Sheets

Related U.S. Application Data

(60) Provisional application No. 61/683,869, filed on Aug. 16, 2012, provisional application No. 61/683,867, filed on Aug. 16, 2012, provisional application No. 62/311,767, filed on Mar. 22, 2016.

(51) Int. Cl.
*A61B 5/00* (2006.01)
*G16H 20/70* (2018.01)
*A61B 5/11* (2006.01)
*G16H 10/20* (2018.01)
*G16H 10/65* (2018.01)
*A61B 5/0205* (2006.01)

(52) U.S. Cl.
CPC .......... *A61B 5/6898* (2013.01); *A61B 5/7235* (2013.01); *G16H 20/70* (2018.01); *G16H 50/50* (2018.01); *A61B 5/0205* (2013.01); *A61B 5/11* (2013.01); *A61B 5/4809* (2013.01); *A61B 5/4815* (2013.01); *A61B 5/4818* (2013.01); *A61M 2205/3303* (2013.01); *A61M 2205/3553* (2013.01); *A61M 2205/3584* (2013.01); *A61M 2205/3592* (2013.01); *A61M 2205/502* (2013.01); *A61M 2205/505* (2013.01); *A61M 2230/63* (2013.01); *G06F 19/325* (2013.01); *G16H 10/20* (2018.01); *G16H 10/65* (2018.01)

(56) References Cited

U.S. PATENT DOCUMENTS

| | | | |
|---|---|---|---|
| 7,246,677 B2 | 7/2007 | Fredriksson et al. | |
| 7,248,677 B2 | 7/2007 | Randall et al. | |
| 7,337,158 B2 | 2/2008 | Fratkina et al. | |
| 7,376,700 B1 | 5/2008 | Clark et al. | |
| 7,584,166 B2 | 9/2009 | Grichnik | |
| 7,761,309 B2 | 7/2010 | Sacco et al. | |
| 7,914,468 B2 | 3/2011 | Shalon et al. | |
| 8,160,901 B2 | 4/2012 | Heywood et al. | |
| 8,500,635 B2 | 8/2013 | Zilca et al. | |
| 8,622,900 B2 | 1/2014 | Jain et al. | |
| 8,684,922 B2 | 4/2014 | Tran | |
| 9,019,106 B2 | 4/2015 | Alameh et al. | |
| 9,286,442 B2 | 3/2016 | Csoma et al. | |
| 9,294,403 B2 | 3/2016 | Mejia et al. | |
| 9,684,922 B2 | 6/2017 | Elberbaum | |
| 2002/0198473 A1 | 12/2002 | Kumar et al. | |
| 2004/0078223 A1 | 4/2004 | Sacco et al. | |
| 2004/0225340 A1 | 11/2004 | Evans | |
| 2005/0020903 A1 | 1/2005 | Krishnan et al. | |
| 2005/0055321 A1 | 3/2005 | Fratkina et al. | |
| 2005/0108051 A1 | 5/2005 | Weinstein | |
| 2005/0169446 A1 | 8/2005 | Randall et al. | |
| 2006/0064037 A1 | 3/2006 | Shalon et al. | |
| 2007/0094048 A1 | 4/2007 | Grichnik | |
| 2007/0226012 A1 | 9/2007 | Salgado et al. | |
| 2007/0288266 A1 | 12/2007 | Sysko et al. | |
| 2008/0059570 A1 | 3/2008 | Bill | |
| 2009/0125333 A1 | 5/2009 | Heywood et al. | |
| 2010/0082367 A1 | 4/2010 | Hains et al. | |
| 2010/0203876 A1 | 8/2010 | Krishnaswamy | |
| 2011/0009715 A1 | 1/2011 | O'Reilly et al. | |
| 2011/0066036 A1 | 3/2011 | Zilca et al. | |
| 2011/0119212 A1 | 5/2011 | De et al. | |
| 2011/0125238 A1* | 5/2011 | Nofzinger | A61F 7/0085 607/109 |
| 2011/0184250 A1 | 7/2011 | Schmidt et al. | |
| 2011/0245633 A1* | 10/2011 | Goldberg | A61B 5/165 600/301 |
| 2012/0053425 A1 | 3/2012 | Michelson et al. | |
| 2012/0289791 A1 | 11/2012 | Jain et al. | |
| 2013/0004129 A1 | 1/2013 | Zhang | |
| 2013/0042116 A1 | 2/2013 | Sakumoto | |
| 2013/0085758 A1 | 4/2013 | Csoma et al. | |
| 2013/0095459 A1 | 4/2013 | Tran | |
| 2013/0117040 A1 | 5/2013 | James et al. | |
| 2013/0154838 A1 | 6/2013 | Alameh et al. | |
| 2013/0297536 A1* | 11/2013 | Almosni | G16H 50/20 706/12 |
| 2014/0039914 A1 | 2/2014 | Dansereau et al. | |
| 2014/0257439 A1* | 9/2014 | Douglas | A61N 5/0618 607/90 |
| 2015/0187199 A1* | 7/2015 | Chang | A61B 5/048 340/575 |
| 2016/0317781 A1 | 11/2016 | Proud | |

FOREIGN PATENT DOCUMENTS

| | | |
|---|---|---|
| JP | 2010514497 A | 5/2010 |
| JP | 2015514497 A | 5/2015 |
| WO | 085308 | 7/2008 |
| WO | 2008085308 A1 | 7/2008 |
| WO | 096634 | 8/2008 |
| WO | 025622 | 3/2012 |
| WO | 003247 | 1/2015 |

OTHER PUBLICATIONS

Thomee, Sara, et al., "Mobile phone use and stress, sleep disturbances, and symptoms of depression among young adults—a prospective short study", BMC Public Health, Biomed Central, London, GB, vol. 11, No. 1, Jan. 31, 2011, p. 66.

Yen, Cheng-Fang, et al., "Symptoms of problematic cellular phone use, functional impairment and its association with depression among adolescents in Southern Taiwan", Journal of Adolescence, Academic Press, Amsterdam, NL, vol. 32, No. 4, Aug. 1, 2009, pp. 863-873.

\* cited by examiner

METHOD AND SYSTEM FOR CHARACTERIZING AND/OR TREATING POOR SLEEP BEHAVIOR

CROSS-REFERENCE TO RELATED APPLICATIONS

This application is a continuation-in-part of U.S. application Ser. No. 13/969,349 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application additionally claims the benefit of U.S. Provisional Application No. 62/311,767 filed 22 Mar. 2016, which is incorporated in its entirety by this reference.

TECHNICAL FIELD

This invention relates generally to the field of mental health and more specifically to a new and useful method and system for characterizing and treating poor sleep behavior in the field of health.

BACKGROUND

An individual's ability to sleep properly can have a profound impact on the individual's functionality, mood, and health. Individual episodes of poor sleep can be disruptive in one's daily life, and over time, prolonged periods of sleep deprivation can interfere with one's ability to physically work and can adversely affect one's mental state. Furthermore, other disorders (e.g., mental health disorders, pain-related disorders, etc.) can be comorbid with sleep disorders, where episodes of poor sleep can have an adverse effect on one's state in relation to another disorder, leading to a negative feedback loop in state across the disorders. Unfortunately, current standards of detection, diagnosis, and treatment of sleep-related disorders, as well as barriers to seeking diagnosis and treatment, are responsible for delays in diagnoses of disorders and/or misdiagnoses of disorders, which cause such disorders to remain untreated. Furthermore, sleep disorders are often treated as "non-serious", which can create social barriers to seeking help and/or promote individuals to self-treat their disorders with various methods of treatment. Current methods of detection, diagnosis, and treatment of sleep disorders are, however, severely deficient in many controllable aspects. In addition to these deficiencies, further limitations in detection, diagnosis, treatment, and/or monitoring of progress during treatment prevent adequate care of individuals with diagnosable and treatable sleep-related disorders.

As such, there is a need in the field of mental health for a new and useful method and system for characterizing and treating poor sleep behavior. The technology includes such a new and useful method and system for characterizing and treating poor sleep behavior.

DESCRIPTION OF THE EMBODIMENTS

The following description of the embodiments of the invention is not intended to limit the invention to these embodiments, but rather to enable any person skilled in the art to make and use this invention.

1. Overview

As shown in FIGS. 1A-1B, 2, and 4, an embodiment of a method 100 for improving sleep characterization and/or a sleeping-related disorder for a user associated with a sleep session includes: receiving a log of use dataset corresponding to user digital communication behavior at a mobile device, the log of use dataset associated with the sleep session (e.g., sleeping period) S110; receiving a supplementary dataset (e.g., motion supplementary dataset) characterizing activity of the user and/or mobile device, the supplementary dataset associated with the sleep session S120; characterizing a sleep-related parameter for the user based on at least one of the log of use dataset and the supplementary dataset S150; determining a sleep care plan for the user based on the sleep-related parameter, the sleep care plan including a therapeutic intervention S160; and promoting a therapeutic intervention to the user according to the sleep care plan S170. In variations, determining the sleep care plan and/or promoting the therapeutic intervention can be performed automatically with the sleep characterization system, performed and/or facilitated by a care provider (e.g., verifying and/or modifying an automatically determined sleep care plan and/or therapeutic intervention), and/or by any suitable entity. The method wo can additionally or alternatively include: receiving a device event dataset characterizing operational states of the mobile communication device within the time period S130 receiving a survey dataset S140 determining one or more user subgroups S180 and/or any other suitable operations.

Figure 7:
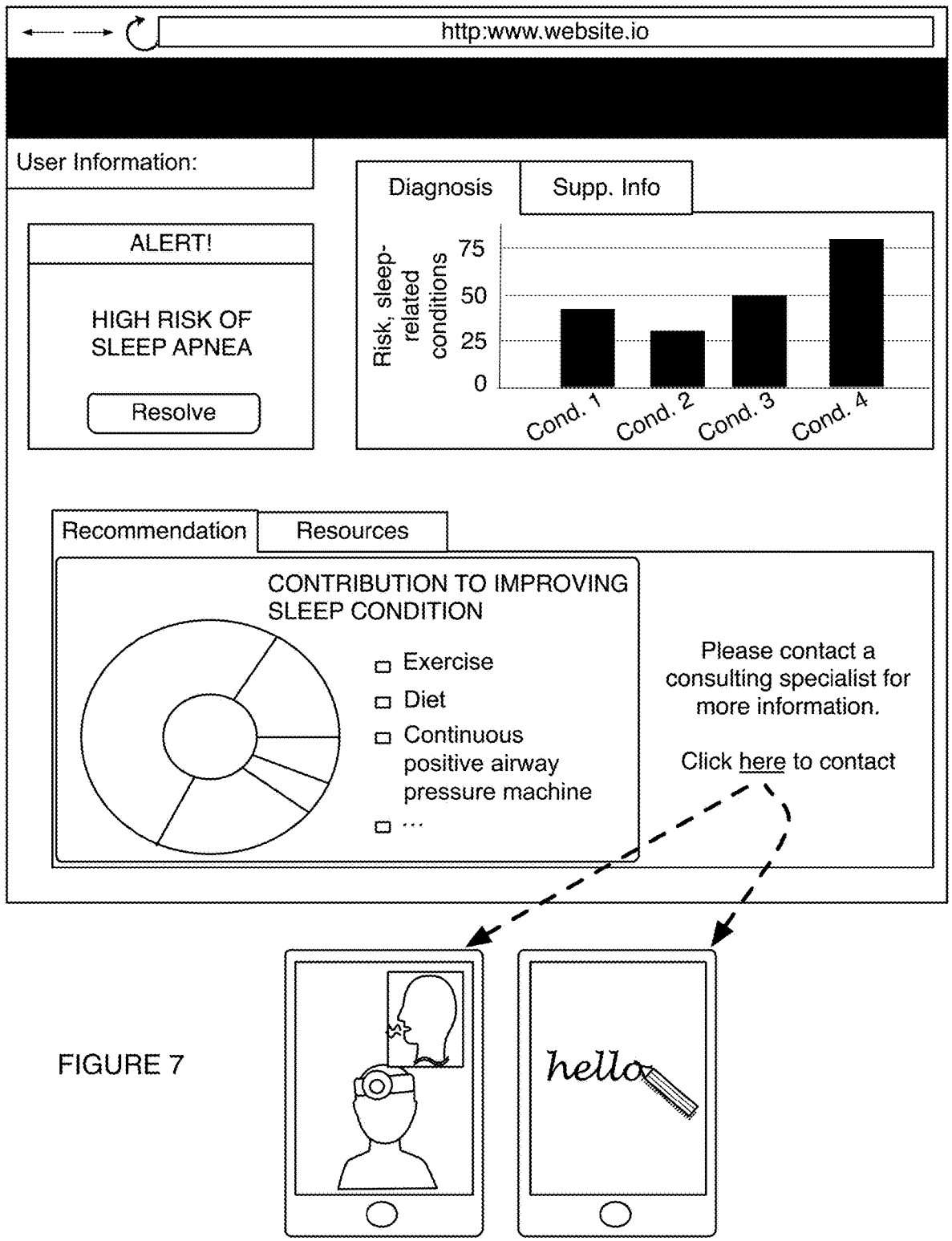
FIG. 7 illustrates an example sleep-related notification.

The method 100 and/or system 200 function to analyze mobile device states, communication behavior (e.g., digital communication behavior in relation to a mobile device of the user), mobility behavior (e.g., locations frequented by the user; physical activity parameters; motion behavior; etc.), and/or other information regarding a user (e.g., patient, at-risk user) potentially experiencing poor sleep, in order to characterize past and/or present sleep behavior of the user. Variations of the method 100 and/or system 200 can further be used to predict future sleep behavior of the user, in assessing risk that the user will experience adverse effects of a sleep disorder without intervention (e.g., as shown in FIG. 7). In a specific application, the method wo can monitor and analyze device events, communication behavior, mobility behavior, and/or other behavior detected from any other suitable sensor(s) associated with a user over time, and promote interventions to the user configured to improve the user's sleep behavior. The therapeutic intervention model can thus be used to drive automated or manual targeted intervention for a user (e.g., via a phone call, email, health tip notification, insight, other electronic communication, other electronic device-based messaging, other electronic device-based notifications, etc.) suffering from poor sleep.

As such, variations of the method 100 and/or system 200 can be implemented in characterizing and/or improving sleep-related conditions including one or more of: jet lag, narcolepsy, night terror, sleep walking, sleep apnea (e.g., obstructive sleep apnea, central sleep apnea, complex sleep apnea syndrome, etc.), restless legs syndrome, bruxism, delayed sleep phase disorder, hypopnea syndrome, insomnia, Kleine-Levin syndrome, nocturia, parasomnias, periodic limb movement disorder, rapid eye movement disorder, shift work sleep disorder, sleep paralysis, somniphobia, catathrenia, idiopathic hypersomnia, conditions associated with sleep-related conditions (e.g., alcoholism, mood disorders, anxiety disorders, panic, psychosis, etc.), and/or any other suitable sleep-related conditions. In relation to depression and/or anxiety (and/or other mental health-related disorders), which can be comorbid with sleep-related disorders, applications of the method wo can be adapted to provide therapeutic interventions to improve sleep behavior in order to improve outcomes and health in relation to states of depression and/or anxiety of the user.

Information derived from a population of users can be used to provide additional insight into connections between a user's behavior and risk of experiencing poor sleep, due to aggregation of data from a population. In a specific example, the method 100 involves a population of users between 18 and 22 years of age, each user having a mobile communication device (e.g., smart phone, tablet, wearable computing device, etc.) and living in an academic environment. However, variations of the specific example can alternatively include users of any other suitable demographic or condition. For instance, non-college-aged users can be included in variations of the method 100 adapted for general population modeling in relation to behavior and sleep-related condition, and patients suffering from other ailments can be included in variations of the method 100 adapted for analysis of users suffering from disorders that are comorbid with sleep disorders.

The method 100 is preferably implemented at least in part by an embodiment of the system 200 described in Section 4 below, but can additionally or alternatively be implemented at any suitable components. Additionally or alternatively, one or more instances of the method 100 and/or processes described herein can be performed asynchronously (e.g., sequentially), concurrently (e.g., in parallel; concurrently on different threads for parallel computing to improve system processing ability for characterizing and/or promoting therapeutic interventions for sleep-related condition; etc.), in temporal relation to a trigger event, and/or in any other suitable order at any suitable time and frequency by and/or using one or more instances of the system 200, elements, and/or entities described herein. However, the method 100 and/or system 200 can be configured in any suitable manner.

2. Benefits

The technology can overcome several challenges faced by conventional approaches in characterizing and/or promoting therapeutic interventions for sleep-related conditions. First, conventional approaches to characterizing sleep-related conditions can require users to visit a care provider (e.g., physicians, sleep specialists, sleep consultants, etc.) and/or sleep testing laboratories (e.g., which can require overnight sleep experiments to characterize a sleep-related condition, etc.). Second, conventional sleep characterization approaches can be inaccurate, such as due to failing to account for unique user behaviors (e.g., digital communication behaviors, mobility behaviors, etc.), for natural conditions (e.g., where conventional approaches can be limited to sleep characterization in unnatural settings), data collection limitations (e.g., quantity of users from which data is collected; amount of data collected per user; rate of data collection; etc.). Third, conventional sleep care plans and/or therapeutic interventions for improving sleep-related conditions can be inconvenient, invasive, and/or impersonalized to the user and their user behaviors. Examples of the method 100 and/or system 200 can confer technologically-rooted solutions to at least the challenges described above.

First, the technology can confer improvements in computer-related technology (e.g., digital communication behavior analytics, computationally-based sleep characterization, digital administration of therapeutic interventions for sleep-related conditions, artificial intelligence, etc.) by facilitating computer performance of functions not previously performable. For example, the technology can improve sleep characterization and treatment through leveraging passively collected digital communication data (e.g., text messaging features, phone calling features) and/or supplementary data (e.g., mobility behavior data extracted from GPS sensors of mobile devices) that would not exist but for advances in mobile devices (e.g., smartphones) and associated digital communication protocols (e.g., WiFi-based phone calling). As such, the technology can, in examples, unobtrusively evaluate and treat sleep-related conditions by continuously gathering a plethora of data that can be used to personalize sleep parameter characterizations and sleep care plans for a user and associated changes in behavior over time, while requiring a minimal or otherwise reduced amount of effort by a patient. In a specific example, the technology can enable data collection for users in their natural sleep setting (e.g., their home), which can enables extraction of insights into differences in sleep patterns due to natural conditions (e.g., sleeping in the same bed with a partner, interactions with family, daily routines, digital activity over time, etc.), rather than, for example, laboratory conditions (e.g., which can also be monitored by the technology).

Second, the technology can confer improvements in computer-related technology through an inventive distribution of functionality across a network including a sleep characterization system (e.g., a remote computing system receiving and analyzing digital communication data across a plurality of users), a plurality of mobile devices (e.g., associated with users possessing a diversity of sleep-related conditions and behaviors), a treatment system (e.g., operable to promote one or more therapeutic interventions to the users, such as at the plurality of mobile devices), and/or other suitable components. For example, the sleep characterization system can include functionality of analyzing digital communication data previously unused for sleep characterization, such as digital communication data derived from a population of users (e.g., patients) and usable for providing insight into connections between a user's digital communication behavior and sleep-related conditions. Such data and insights can subsequently be used to provide, evaluate, and/or subsequently update therapeutic interventions for each user in a tailored, dynamically modifiable sleep care plan, the personalization of which can improve user engagement with the sleep care plan. As such, the technology can provide a centralized, full-stack approach to digitally monitoring the physiological and psychological sleep-related health of a patient, leading to improved efficiency of care delivery, cost savings, and care delivery scalability.

Third, the technology can confer improvements in computer-related technology through computer-implemented rules (e.g., feature engineering rules; therapeutic intervention rules; etc.). The increasing prevalence of user digital communication across a plurality of communication protocols can translate into a plethora of digital communication data, giving rise to questions of how to process and analyze the vast array of data, such as for generating actionable sleep-related insights. However, the technology can address such challenges by, for example, applying feature engineering rules in generating features (e.g., digital communication-mobility behavior features) operable to improve processing speed and/or accuracy of sleep characterization and/or treatment (e.g., to enable real-time sleep characterization and/or real-time provision of therapeutic interventions).

Fourth, the technology can improve the technical fields of at least digital communication, computational modeling of user behavior and/or sleep-related conditions, digital medicine, and/or other relevant fields. The technology can continuously collect and utilize specialized datasets unique to internet-enabled, non-generalized mobile devices in order to characterize and/or treat sleep-related conditions. Further, the technology can take advantage of such datasets to better improve the understanding of correlations between patient digital communication behavior, sleep-related conditions, and appropriate therapeutic interventions.

Fifth, the technology can transform entities (e.g., mobile devices, treatment system including medical devices, users, etc.) into different states or things. For example, the technology can automatically initiate provision of therapeutic interventions to the user, such as by activating and/or controlling one or more treatment systems (e.g., supplementary sleep-related devices, mobile communication devices; etc.) to promote the therapeutic interventions. In a specific example, the technology can activate an application executing on a smart phone in automatically providing a sleep-related notification (e.g., recommending that the user minimizes mobile device usage, etc.) in response to sleep-related threshold conditions. In another example, the technology can determine therapeutic interventions to promote to a patient to modify user sleep behaviors in improving sleep-related conditions of the patient, thereby transforming the sleep-related condition and the health of the patient.

Sixth, the technology can provide technical solutions necessarily rooted in computer technology (e.g., utilizing computational models for extracting sleep-related parameters based on a user's unique behaviors; dynamically generating and modifying digital sleep care plans including digitally promoted therapeutic interventions, such as sleep-related notifications including hyperlinks to sleep-related content; modifying visually perceptible elements associated with therapeutic interventions to improve, for example, display of the sleep-related notifications in accordance with treating sleep-related conditions; etc.) to overcome issues specifically arising with computer technology (e.g., negative correlations between sleep quality and computer technology usage; modifying elements associated with user interfaces of computer technology to improve sleep-related conditions, such as through modifying display of content).

Seventh, the technology can leverage specialized computing devices (e.g., mobile devices with mobility-related sensors, physical activity monitoring capabilities, digital communication behavior-monitoring capabilities, sleep-related sensors, ambient environment sensors, supplementary sleep-related devices) in sleep characterization and/or treatment. The technology can, however, provide any other suitable benefit(s) in the context of using non-generalized computer systems for characterizing and/or promoting therapeutic interventions for sleep-related conditions.

3.1 Method—Receiving a Log of Use Dataset

Block S110 recites: receiving a log of use dataset corresponding to user digital communication behavior at a mobile device (e.g., mobile communication device), the log of use dataset associated with a sleep session. Block S110 functions to unobtrusively collect and/or retrieve communication-related data from a user's mobile communication device. The log of use dataset preferably includes a log of use of a communication application (e.g., native communication application, phone calling application, messaging application, social media application, etc.) executing on a mobile communication device of the user within a time period (e.g., a sleep session), but can additionally or alternatively include logs of use (e.g., user inputs such as taps, swipes, key presses, etc.) of any suitable application.

Regarding Block S110, a sleep session (e.g., sleeping period) preferably includes at least one time period when the user is sleeping, but can additionally or alternatively include time periods when the user is awake (e.g., a time window where the user wakes up to go to the bathroom in between time windows of sleeping, etc.). The parameters of a sleep session (e.g., the start and end of the sleep session) can be defined by any one or more of: user input (e.g., defining the start of and end of a sleep session as the times specified by the user); a predetermined time range from when the user falls asleep (e.g., defining the start of a sleep session as 10 minutes prior to when the user falls asleep) and/or when the user wakes up (e.g., defining the end of the sleep session as 10 minutes after the user leaves their bed as determined by mobile device location data; etc.); inferred sleep times and awake times (e.g., based on the motion supplementary dataset indicating the user entering their bedroom at a time within 1 hour of their average time of falling asleep; inferring a fall asleep time based on a cessation of digital communication; etc.); historical sleep times and/or awake times (e.g., average time at night that the user falls asleep), sleep sessions of other users (e.g., average time of falling asleep for a user subgroup sharing a sleeping-related characteristic, etc.); predetermined times (e.g., a sleep session start at 9:00 pm everyday, and an end at 6:00 am everyday); device events (e.g., defining a start of a sleep session as the time at which a user opens a sleep-related application on the mobile device; defining sleep session parameters based on tap gestures; lock actions; unlock actions; charging; application initiation; application termination; type of applications, etc.); and/or any other suitable criteria. Sleep sessions are preferably associated with a single user, but can additionally or alternatively be associated with multiple users (e.g., a pair of users sleeping in the same bed, etc.). Sleep sessions are preferably associated with one or more dates (e.g., February 20; September 4 to 5, etc.), but can be associated with any suitable temporal parameter and/or other data. Sleep sessions can span seconds, minutes, hours, days, and/or any other suitable time unit. However, sleep sessions can include any suitable times, and/or be defined in any suitable manner (e.g., associated with any suitable datasets described in relation to Block S110-S140).

Preferably, Block S110 is implemented using a module of a processing subsystem configured to interface with a native data collection application executing on a mobile communication device (e.g., smartphone, tablet, personal data assistant, personal music player, vehicle, head-mounted wearable computing device, wrist-mounted wearable computing device, etc.) of the user. As such, in one variation, a native data collection application can be installed on the mobile communication device of the user, can execute substantially continuously while the mobile communication device is in an active state (e.g., in use, in an on-state, in a sleep state, etc.), and can record communication parameters (e.g., communication times, durations, contact entities) of each inbound and/or outbound communication from the mobile communication device. In implementing Block S110, the mobile communication device can then upload this data to a database (e.g., remote server, cloud computing system, storage module), at a desired frequency (e.g., in near real-time during a sleep session, every hour, at the end of each day, etc.) to be accessed by the processing subsystem. For example, Block S110 can include, in response to detecting the start of a sleep session (e.g., 30 minutes prior to an average bedtime of the user), logging digital communications (e.g., time, frequency, content, participants, application, etc.) into a log of use; and streaming the corresponding log entries to a remote sleep characterization system in substantially real-time (e.g., where the log of use can be subsequently processed in other Blocks of the method 100).

As such, Block S110 preferably enables collection of one or more of: phone call-related data (e.g., number of sent and/or received calls, call duration, call start and/or end time, location of the user before, during, and/or after a call, and number of and time points of missed or ignored calls); text messaging (e.g., SMS test messaging) data (e.g., number of messages sent and/or received, message length associated with a contact of the user, message entry speed, delay between message completion time point and sending time point, message efficiency, message accuracy, time of sent and/or received messages, location of the user when receiving and/or sending a message); data on textual messages sent through other communication venues (e.g., public and/or private textual messages sent to contacts of the user through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments) and any other suitable type of data. However, collecting a log of use dataset Siio can be performed in any suitable manner.

3.2 Method—Receiving a Supplementary Dataset

Block S120 recites: receiving a supplementary dataset characterizing activity of the user in association with the time period, which functions to unobtrusively receive non-communication-related data from a user's mobile communication device and/or other device configured to receive contextual data from the user. Block S120 can include receiving non-communication-related data pertaining to the user before, during, and/or after (or in the absence of) communication with another user (e.g., a phone call) and/or computer network (e.g., a social networking application), as described above in relation to Block S110. Block S120 can additionally or alternatively include receiving data associated with user activity from one or more application programming interfaces (APIs) configured to provide user-specific activity information (e.g., a Google API for user activity, an Apple Health Kit API, etc.).

In some variations, Block S120 can include receiving one or more of: location information, movement information (e.g., related to physical isolation, related to lethargy), device usage information (e.g., screen usage information, physical movement of the mobile communication device, etc.), device authentication information (e.g., information associated with authenticated unlocking of the mobile communication device), and/or any other suitable information. For instance, the supplementary dataset can include a motion supplementary dataset including a log of times when the user has picked up and/or placed the mobile communication device down, in able to determine when the mobile communication device was in use. Such data can be used to flag certain time periods as time periods where the user was awake. In variations, Block S120 can include receiving a motion supplementary dataset including location information of the user by way of one or more of: receiving a GPS location of the user (e.g., from a GPS sensor within the mobile communication device of the user), estimating the location of the user through triangulation of local cellular towers in communication with the mobile communication device, identifying a geo-located local Wi-Fi hotspot during a phone call, and in any other suitable manner. In a specific example, Block S120 can include collecting a motion supplementary dataset associated with a sleep session, such as including one or more of: user location data (e.g., a user located in the living room instead of a bedroom during a sleep session, etc.), physical activity data (e.g., footstep parameters; heart rate above a threshold amount exceeding an average resting heart rate while sleeping; accelerometer and/or gyroscope data; breathing patterns; other cardiovascular and/or physical activity parameters; etc.), and/or any other suitable data. In applications, data received in Block S110 and S120 can be processed to track behavior characteristics of the user, such as mobility, periods of isolation, quality of life (e.g., work-life balance based on time spent at specific locations), and any other location-derived behavior information.

In some variations, Block S120 can include collecting sleep-related parameters associated with sleep-related conditions, such as from electronic health records, sensors of mobile devices and/or supplementary sleep-related devices, user inputs (e.g., entries by the user at the mobile device), and/or other suitable sources. Sleep-related parameters can include one or more of: electroencephalogram (EEG) data, electrooculogram (EOG) data, electromyogram (EMG) data, electrocardiogram (ECG) data, airflow data (e.g., nasal airflow, oral airflow, measured by pressure transducers, thermocouples, etc.), pulse oximetry data, sound probes (e.g., to measure snoring), polysomnography data, family conditions, genetic data, microbiome data, and/or any other sleep-related data.

Variations of Blocks S110, S120, and/or other Blocks (e.g., S130, S140) of the method 100 can thus enable, after processing of their respective data outputs, identification of sleeping periods and awake periods of the user, and/or any other suitable sleep-related parameters. Furthermore, variations of Blocks S110 and/or S120 can be implemented in manners analogous to those described in U.S. application Ser. No. 14/839,053 entitled "Method for Modeling Behavior and Depression State" and filed on 28 Aug. 2015 and U.S. application Ser. No. 14/839,232 entitled "Method for Modeling Behavior and Psychotic Disorders" and filed on 28 Aug. 2015, which are each incorporated in its entirety by this reference. Variations of the method 100 can, however, omit any one or more of Blocks S110, S120, and/or other portions of the method 100 in modeling sleep behavior of a user and providing therapeutic interventions to the user. However, collecting supplementary datasets can be performed in any suitable manner.

3.3 Method—Receiving a Device Event Dataset

Some variations of the method 100 can include Block S130, which recites: receiving a device event dataset characterizing operational states of the mobile communication device within the time period. Block S130 functions to provide device event data as an input into a model for characterizing sleep-related parameters (e.g., identifying periods when the user is asleep and/or when the user is awake), determining therapeutic interventions, and/or promoting therapeutic interventions. The device event dataset can include data associated with changes in states of the device, such that a change in device state triggers transmission of device event data to the sleep characterization system in Block S130. Additionally or alternatively, the device event dataset can be associated with sampling (e.g., regular sampling, intermittent sampling, random sampling, etc.) of device event information stored in a log at the mobile communication device, such that Block S130 includes receiving a dataset including a set of time points and one or more aspects of device state at each of the set of time points. In a specific example, sampling of a log of device events of the mobile communication device can be performed at a sub-minute frequency; however, in variations of the specific example, the log can be sampled at any other suitable frequency.

In variations of Block S130 the device event data can provide time points of device events associated with one or more of: device charging (e.g., the device has transitioned to or from a charging state; etc.), device powering (e.g., the device has transitioned between a powered off state and a powered on state; etc.), device idling (e.g., the device has transitioned between an active state and an idling state; etc.), intelligent personal assistant activation (e.g., activation of Apple Siri, activation of Google Now, activation of Windows Cortana, activation of Amazon Echo, etc.), alarm clock states (e.g., alarm clock on state, alarm clock off state, alarm clock snoozing state, etc.), audio output device state (e.g., music application activity state), video output device state (e.g., video application activity state), media casting state (e.g., music/video being cast to other devices, such as Chromecast, Miracast, Airplay devices, etc.), sensor activation state (e.g., initiation and/or cessation of sampling of sensor measurements, types of sensors activated, etc.), communicative state (e.g., connectivity, transmission, receiving, etc.), Bluetooth connectivity state in relation to other devices (e.g., a wireless alarm clock), and any other suitable device event. Additionally or alternatively, the device event data can include data from sensors (e.g., accelerometer, gyroscope, other motion sensors, other biometric sensors, etc.) implemented with the mobile device, as described in U.S. application Ser. No. 13/969,339 entitled "Method for Modeling Behavior and Health Changes" and filed on 16 Aug. 2013. However, collecting device event datasets S130 can be performed in any suitable manner.

3.4 Method—Receiving a Survey Dataset

As shown in FIGS. 1A-1B, 2, and 4, some variations of the method 100 can include Block S140 which recites: receiving a survey dataset (e.g., included in a supplementary dataset) including responses, to at least one of a set of sleep-assessment surveys, associated with a set of time points of the time period, from the user. Block S140 can function to provide survey data associated with a specific time point, time period (e.g., sleep session), and/or other suitable time unit in the life of the user and/or associated users (e.g., a partner sleeping in the same bed with a user; a parent with the same sleeping schedule as their child; etc.). Block S140 can additionally or alternatively be used to aggregate survey data from the user over time, in order to generate a personalized model of the user's behavior from self-reported data. Block S140 can additionally or alternatively be used to aggregate survey data from a population of users, in order to generate a population model of behavior for a population of users. As such, personalized and/or population-wide models can be used to inform assessments of sleep for each of a population of users (e.g., in terms of estimating sleep-related parameters for a user). The survey dataset can include interview and/or self-reported information from the user. Furthermore, the survey dataset preferably includes quantitative data, but can additionally or alternatively include qualitative data pertaining to a sleep-related condition of the user corresponding to at least a subset of the set of time points. Furthermore, while portions of the survey dataset preferably correspond to time points within the time period of Block S110, portions of the survey dataset can alternatively correspond to time points outside of the time period of Block S110 (e.g., as in a pre-screening or a post-screening survey). Additionally or alternatively, Block S140 can include receiving clinical data (e.g., information gathered in a clinic or laboratory setting by a clinician) and/or any other suitable data.

In Block S140 the set of time points can include uniformly or non-uniformly-spaced time points, and can be constrained within or extend beyond the time period of the log of use of the communication application of Block S110. As such, in variations, the set of time points can include regularly-spaced time points (e.g., time points spaced apart by an hour, by a day, by a week, by a month, etc.) with a suitable resolution for enabling detection of transitions between awake states and asleep states of the user. Additionally or alternatively, provision of a survey and/or reception of responses to a survey can be triggered upon detection of an event of the user (e.g., based upon data from sensors associated with the user, based upon an output of an analysis of subsequent blocks of the method 100, etc.) or any other suitable change in state of the user. Furthermore, for all time points of the set of time points, an identical subset of the set of sleep-assessment surveys can be provided to the user; however, in alternative variations, different subsets of the set of sleep-assessment surveys can be provided to the user at different time points of the set of time points.

In variations of Block S140 the survey dataset can include responses to surveys configured to assess or validate values of one or more sleep-related parameters intended to be determined using the method 100. While the survey(s) can be provided such that the user is prompted to provide quantitative answers, the survey(s) can additionally or alternatively be provided such that qualitative information provided by the user is transformed into quantitative data according to a response-scoring algorithm. In examples, the set of sleep-assessment surveys can include surveys derived from one or more of: a behavioral risk factor surveillance system (BRFSS) questionnaire, a youth risk behavior survey (YRBS), a national health interview survey (NHIS), a national health and nutrition examination survey (NHANES), and any other suitable sleep survey. However, the set of surveys can include any other suitable surveys or adaptations thereof. As such, the survey dataset can include quantitative scores of the user for one or more subsets of surveys for each of the set of time points (or a subset of the set of time points).

In examples of Block S140 the survey dataset can include responses (e.g., weekly responses for a period of 6 months) to survey configured to assess sleep patterns in terms of one or more of: self-assessed sleep times, self-assessed waking times, self-assessed sleep quantity (e.g., sleep duration), self-assessed sleep quality (e.g., amount of non-rapid eye movement sleep; amount of rapid eye movement sleep; light sleep; deep sleep; etc.), self-assessed difficulty in falling asleep, and self-assessed daytime drowsiness, assessments from associated users (e.g., guardians, partners, etc.), sleep-related symptoms (e.g., energy levels; headaches; psychological conditions such as depression; swelling; nocturnal urination; gasping; choking; coughing; reflux; irregular breathing; etc.), sleep-related risk factors (e.g., demographics, weight, digital communication behaviors, mobility behaviors such as physical activity, smoking, family history, etc.), and/or other suitable sleep-related parameters. In variations of the example, the survey dataset includes responses to a survey configured to assess one or more of: workload (e.g., academic workload, job workload, home environment workload, etc.), stress levels, and any other suitable information relevant to or potentially affecting sleep behavior.

Variations of Blocks S140 can thus enable, after processing of their respective data outputs, identification of sleep-related parameters including periods and awake periods of the user. Furthermore, variations of Block S130 can be implemented in manners analogous to those described in U.S. application Ser. No. 14/839,053 entitled "Method for Modeling Behavior and Depression State" and filed on 28 Aug. 2015 and U.S. application Ser. No. 14/839,232 entitled "Method for Modeling Behavior and Psychotic Disorders" and filed on 28 Aug. 2015. Variations of the method 100 can, however, omit Block S140 in modeling sleep behavior of a user and providing interventions to the user. However, collecting a survey dataset S140 can be performed in any suitable manner.

Blocks S110-S140 can thus provide passive data (e.g., unobtrusively collected data) and/or active data (e.g., survey data) that can be taken as inputs in Block S150 in order to generate analyses pertaining to present, past, and/or future sleep-related states of a user. Additionally or alternatively, Blocks S110-S140, can be performed in any manner analogous to U.S. application Ser. No. 13/969,339 entitled "Method for Modeling Behavior and Health Changes" and filed on 16 Aug. 2013, which is incorporated in its entirety herein by this reference.

3.5 Method—Characterizing a Sleep-Related Parameter

Figure 8:
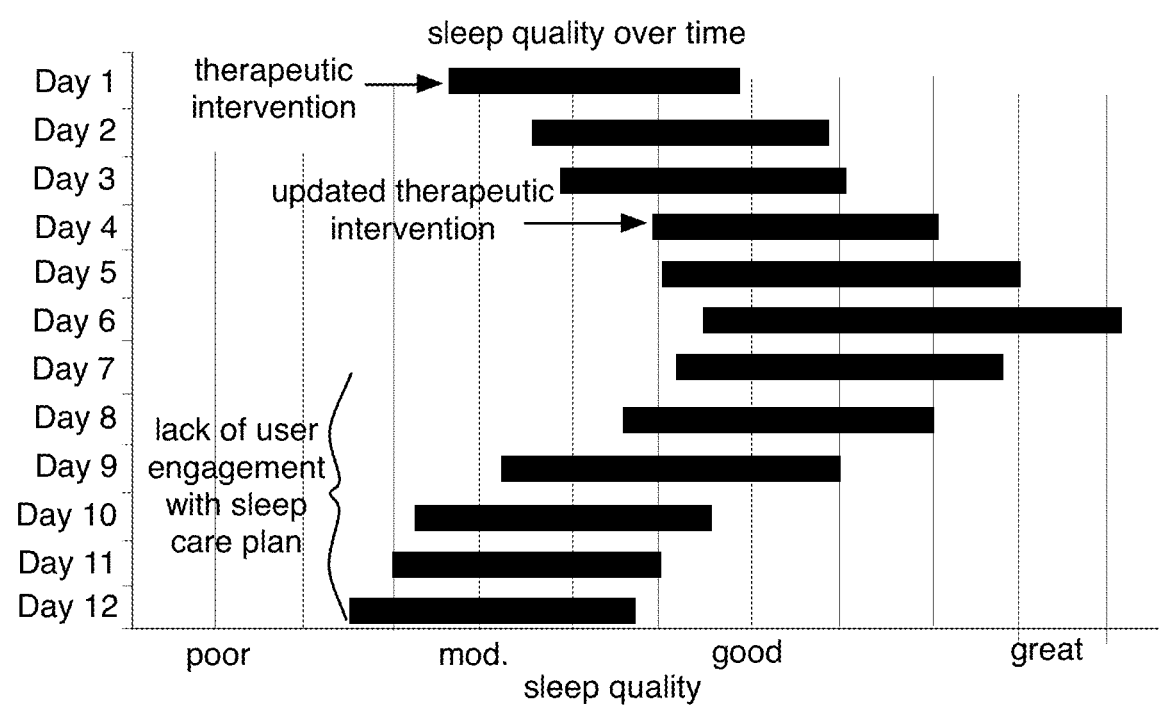
FIG. 8 illustrates an example sleep-related notification.

Block S150 recites: characterizing one or more sleep-related parameters (e.g., a series of sleep-related parameters descriptive of sleep quality at times spanning the sleep session and/or multiple sleeping sessions, as shown in FIG. 8; etc.) for the user based on at least one of the log of use dataset and the supplementary dataset (and/or a device event dataset, a survey dataset, and/or other suitable data). Block S150 functions to process information from the dataset(s) of one or more of Blocks S110-S140 in order to generate values of sleep-related parameters associated with the time period (e.g., sleep session), where the sleep-related parameters (e.g., sleeping parameters) can include any one or more of: a set of sleeping periods (e.g., a start time and an end time of each of a set of sleeping periods), a set of awake periods (e.g., a start time and an end time of each of a set of awake periods), bedtimes, waking times, aggregate sleep time parameters (e.g., total sleep time, average sleep time, median sleep time, etc.), sleep latency, sleep efficiency, awakening parameters (e.g., sleep interruptions; sleep arousals), sleep quality (e.g., in terms of restful vs. restless sleep; rapid eye movement sleep; non-rapid eye movement sleep; different sleep stages; etc.), apnea-hypopnea index (AHI), breathing parameters (e.g., oral airflow; nasal airflow; sleep-disordered breathing; oxygen desaturation; etc.), risk parameters (e.g., risk of exhibiting a sleep-related condition; risk of changes to sleep-related parameter values), diagnosis parameters (e.g., diagnosis of a sleep-related disorders, etc.), cardiovascular parameters (e.g., heart rate, blood pressure, etc.), and/or any other suitable sleep-related parameters of the user.

In a variation of Block S150, determining a sleep-related parameter can be based on one or more log of use datasets. In an example, Block S150 can include characterizing a sleep-related parameter based on an awake period (e.g., defining the length of the awake period based on the length of a phone call that transpired during the sleep session) within the sleep session identified based on digital communication log entries of a log of use recorded during the sleep session (e.g., reducing the calculated total sleeping time by the duration of the awake period). In this or other examples, characterizing a sleep-related parameter and/or other portions of the method 100 (e.g., Blocks S160-S170) can be performed in real-time during the sleep session, such as during the identified awake period in order to prompt the user to develop healthy sleeping habits by providing user feedback in real-time (e.g., reminders that participating in digital communications during a sleeping period can be harmful to sleep quality, etc.). In another example, the method 100 can include: collecting a plurality of log of use datasets corresponding to digital communication behavior of a population of users; identifying a correlation between poor sleep quality (e.g., greater than average sleep latency, greater than average number of sleep interruptions, lower than average amount of rapid eye movement sleep, etc.) and a greater than average amount of digital communication (e.g., increased number of text messages, longer phone call duration, etc.) within 30 minutes of bedtime; and characterizing a poor sleep quality parameter for a current user based on a log of use indicating increased digital communication before bedtime for the current user. In another example, Block S150 can include calculating a number of awakenings during a sleep session based on the number of digital communication sessions (e.g., where at least one digital communication was transmitted from the mobile device) during the sleep session. In another example, characterizing sleep-related parameters can be based on analysis of digital communication content included in the log of use. In a specific example, natural language processing approaches can be applied to text messages transmitted by the user to extract sentiment associated with and informative of sleep-related parameters (e.g., characterizing poor sleep quality based on a text message of "I'm so awake right now" transmitted at a time historically associated with sleeping periods of the user, etc.). However, determining sleep-related parameters based on digital communication behaviors (e.g., as indicated by logs of use) can be performed in any suitable manner.

In another variation of Block S150, characterizing sleep-related parameters can be based on a supplementary dataset. For example, the method 100 can include: sampling location data (e.g., GPS coordinates, indoor positioning system data, etc.) with a location sensor (e.g., GPS sensor of a smartphone, beacons in the bedroom, etc.); receiving the location data at a sleep characterization system; and classifying the user as awake at times when the location data indicates a geographic location of the user outside a threshold distance from the user's sleep location (e.g., bedroom). In another example, the method 100 can include: identifying a correlation between a physical activity parameter (e.g., number of footsteps calculated from a fitness wearable device in communication with the sleep characterization system) and a sleep-related parameter (e.g., correlating a number of footsteps exceeding a threshold as correlated with high sleep quality based on survey responses received for the corresponding days); and characterizing a sleep-related parameter (e.g., sleep quality) for a given day based on the physical activity parameter value for the given day and the identified correlation with the sleep-related parameter. In another example, Block S150 can include determining a sleep quality parameter based on the number and/or degree of sleep arousals determined based on motion sensor data (e.g., gyroscope and/or accelerometer sensor measurements indicating a greater than average amount of tossing and turning during the sleep session) and log of use data (e.g., digital communications transmitted at times within a threshold of the times corresponding to the tossing and turning). In another example, Block S150 can include characterizing breathing parameters based on audio recorded at a microphone of the mobile communication device. However, characterizing sleep-related parameters based on supplementary datasets can be performed in any suitable manner.

In another variation of Block S150, characterizing sleep-related parameters can be based on a device event dataset. For example, Block S150 can include characterizing awake periods based on activations of a mobile device from an idle state to an awake state during a sleep session. In another example, Block S150 can include characterizing sleep quality based on the type of applications engaged with by the user in association with sleeping period (e.g., immediately prior to the sleeping period, during the sleeping period, etc.) and correlations between the types of applications and sleep quality (e.g., correlations of improved sleep quality and user engagement with meditation-related applications prior to a sleep session; correlations of poor sleep quality and user engagement with social media applications during a sleep session; correlations extracted from device event datasets and corresponding sleep-related parameters derived from survey responses; etc.). However, characterizing sleep-related parameters based on device event datasets can be performed in any suitable manner.

In another variation of Block S150, characterizing sleep-related parameters can be based on survey datasets administered prior to, during, and/or after sleep sessions. For example, the method 100 can include identifying correlations between digital communication behaviors and sleep-related parameters based on logs of use and sleep survey responses across a population of users; and generating a sleep characterization model based on the correlations. In another example, characterizing sleep-related parameters for a sleep session can be based on survey responses to a survey administered after and for the sleep session (e.g., calculating a sleep time based on an average of the sleep time specified by the user in the survey response and the sleep time based on a log of use dataset and a supplementary dataset, etc.). However, characterizing sleep-related parameters based on survey data can be performed in any suitable manner.

Figure 3A:
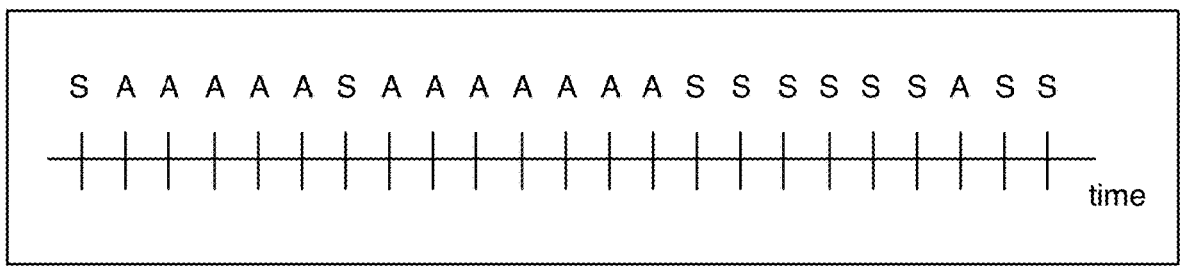
FIGS. 3A-3B depict variations of portions of a method.

In one variation of Block S150, as shown in FIG. 3A, Block S150 can include tagging each of a set of time points of the time period as a time point when the user was awake or when the user was asleep. Tagging a time point as an awake time point can be based upon processing data of one or more of the log of use, the supplementary dataset, the device event dataset, and the survey dataset at the time point and, additionally or alternatively, time points proximal to the time point. For instance, in relation to the log of use, a time point can be tagged as an awake time point if the user was communicating at the time point and/or at time points proximal to the time point. In relation to the supplementary dataset, a time point can be tagged as an awake time point if the user was mobile or at a location not associated with sleep at the time point and/or at time points proximal to the time point. In relation to the device event dataset, a time point can be tagged as an awake time point if the mobile device was in a powered on state and a non-idle state at the time point and/or at time points proximal to the time point. In relation to the survey dataset, a time point can be tagged as an awake time point if the time point is after the self-reported waking time of the user. Each contribution (e.g., log of use contribution, supplementary dataset contribution, device event dataset contribution, survey dataset contribution, etc.) to tagging of a time point as an awake point can be weighted and/or or otherwise combined with other contributions in determining a confidence level in classification of the time point as an awake time point. Furthermore, variations of the above examples can additionally or alternatively omit any contributing factor (e.g., survey dataset contribution, log of use contribution, etc.). In one specific example, tagging can be based solely on contributions from the supplementary dataset of Block S120 and the device event dataset of Block S130.

In relation to Block S150, with regard to classification of a time point as an asleep time point, in relation to the log of use, a time point can be tagged as a sleep time point if the user was not communicating at the time point and/or at time points proximal to the time point. In relation to the supplementary dataset, a time point can be tagged as an asleep time point if the user was non-mobile, was not interacting with the device (e.g., the screen was locked), or was at a location associated with sleep (e.g., at home) at the time point and/or at time points proximal to the time point. In relation to the device event dataset, a time point can be tagged as an asleep time point if the mobile device was in a powered off state, was in an idle state, or was in a charging state at the time point and/or at time points proximal to the time point. In relation to the survey dataset, a time point can be tagged as an asleep time point if the time point is after the self-reported sleep time of the user. Each contribution (e.g., log of use contribution, supplementary dataset contribution, device event dataset contribution, survey dataset contribution, etc.) to tagging of a time point as an asleep point can be weighted and/or or otherwise combined with other contributions in determining a confidence level in classification of the time point as an awake time point. Furthermore, variations of the above examples can additionally or alternatively omit any contributing factor (e.g., survey dataset contribution, log of use contribution, etc.). In one specific example, tagging can be based solely on contributions from the supplementary dataset of Block S120 (e.g., in relation to activity) and the device event dataset of Block S130.

Regarding Block S150, characterizing sleep-related parameters is preferably based on one or more sleep-related features derived from any one or more datasets (e.g., described in Block S110-S140). Feedback features can include any of: textual features (e.g., word frequency, sentiment, punctuation associated with words present in text messages; etc.), graphical features (e.g., emojis used in text messages; media posted to social networking sites; media transmitted and/or received through digital messages; associated pixel values; etc.), audio features (e.g., Mel Frequency Cepstral Coefficients extracted from audio captured by the mobile device during the sleep session and/or phone calls; etc.), cross-user features (e.g., average frequency of text messages; average length and/or duration of phone calls and/or text messaging; users participating in a digital communication; etc.), and/or any other suitable features.

In relation to Block S150, determining sleep-related features is preferably based on one or more computer-implemented rules, such as a feature engineering rule (e.g., feature selection rule; an associated user preference rule; etc.), but sleep-related features can be determined based on any suitable information. Block S150 preferably includes applying computer-implemented rules to process cross-user data (e.g., in extracting features for use in generating a sleep characterization model) as well as user data (e.g., in extracting user-specific feature values for input into the sleep characterization model for outputting sleep-related parameter values, etc.), but can additionally or alternatively include applying computer-implemented rules to extract sleep-related features on a device basis (e.g., generating different features for a first type of mobile device versus a second type of mobile device, based on the types of data collected from the mobile devices, etc.), sleep-related condition basis (e.g., extracting different features from a log of use dataset for a first sleeping-related disorder versus a second sleeping-related disorder, based on the different correlations between different digital communication-related features and the different disorders, etc.), user subgroup basis, and/or any other suitable basis. In an example, the feature engineering rule can include a unit standardization rule, which can standardize a given type of data that can vary in format across mobile devices (e.g., different formats of timestamps associated with log entries in a log of use across different types of mobile devices and/or operating systems; different formats of expressing phone call data and/or text messaging data; etc.), applications executing on the mobile devices, users (e.g., expressing estimated total sleep time in minutes versus hours, etc.), care providers (e.g., varying units for measurements of sleep-related parameters in a medical setting), and/or any other suitable entities.

Relating to Block S150, in another example, applying the feature engineering rule can include generating a feature based on a combination of data. In a specific example, Block S150 can include extracting a set of features from a log of use dataset and a motion supplementary dataset, based on a feature engineering computer-implemented rule operable to improve accuracy of the sleep characterization. In another specific example, Block S150 can include extracting a digital communication-mobility behavior feature (e.g., number of text messages sent by a user geographically located in their primary bed used for sleeping) based on processing a text messaging parameter (e.g., frequency of text messages) from the log of use dataset with a location parameter (e.g., geographic locations associated with the text messages) from the motion supplementary dataset, according to the feature engineering computer-implemented rule. In another specific example, the digital communication-mobility behavior feature can include the phone call duration of phone calls within a predetermined time threshold of a sleep session start time and within a predetermined distance threshold of the user's bedroom.

In another example in relation to Block S150, applying a feature engineering rule can include applying a feature selection rule (e.g., feature selection algorithms such as exhaustive, best first, simulated annealing, greedy forward, greedy backward, and/or other suitable feature selection algorithms) to filter, rank, and/or otherwise select sleep-related features. Feature selection rules can select features based on optimizing for processing speed, accuracy, diagnosis, and/or any other suitable criteria. In another example, Block S150 can include applying a user preference rule. For example user preference rules can include any one or more of: a sleep-related parameter preference rule specifying the sleep-related parameters to be determined for the user (e.g., where Block S150 includes extracting sleeping-related features with highest correlation with the specified sleep-related parameters, etc.); privacy rules specifying the types of data that can be collected from the user (e.g., where Block S150 includes applying feature engineering rules with data requirements met by the types of data collectable from the user); and/or any other suitable rules. Regarding Block S150, sleep-related features and/or associated computer-implemented rules are preferably operable to improve accuracy of sleep characterization (e.g., by identifying, generating, and applying features with the greatest correlations to sleep-related parameters; by selectively reducing the number of features processed in characterizing a sleep-related parameter, etc.). However, determining sleep-related features and/or characterizing sleep-related parameters based on the sleep-related features can be performed in any suitable manner.

Determining sleep-related parameters is preferably performed with a sleep characterization model including any one or more of: probabilistic properties, heuristic properties, deterministic properties, and/or any other suitable properties. In a variation, the sleep characterization model can include weights assigned to different sleep-related features and/or types of sleep-related data. For example, in determining a value for sleep quality, the frequency of text messages during a sleep session can be weighted more heavily than the length of the text messages. In another variation, applying a sleep characterization model can include applying one or more machine learning sleep characterization models employing one or more machine learning approaches including one or more of those described in U.S. application Ser. No. 15/265,454 entitled "Method for Providing Health Therapeutic Interventions to a User" and filed on 14 Sep. 2016, which is herein incorporated in its entirety by this reference, and/or any other suitable form of machine learning algorithm. In a specific example, a training sample can correspond to a single sleep session for a user. The training sample can include digital communication features (e.g., extracted from log of use datasets, etc.), mobility features (e.g., extracted from motion datasets, etc.), and/or other suitable features (e.g., where the feature values are vectorized and/or otherwise processed) and a corresponding label (e.g., a sleep-related parameter value, as determined based on survey datasets including survey responses; biometric sensor measurements taken during the sleep session; and/or any other suitable data). However, applying weights and/or a machine learning sleep characterization models can be performed in any suitable manner.

In another variation of Block S150, different sleep characterization models (e.g., generated with different algorithms, with different sets of features, with different input and/or output types, etc.) can be generated (and/or selected, retrieved, and/or executed) based on any one or more of the criteria described above in relation to the different bases for applying different computer-implemented rules in generating sleeping-related features, and/or on any suitable criteria. For example, different sleep characterization models can be applied in relation to different data types (e.g., a first sleep time characterization model leveraging log of use data; and a second sleep time characterization model leveraging device event data; etc.). In examples, Block S150 can include applying different sleep characterization models in an ensemble approach (e.g., predicting different values for sleep quality using a plurality of sleep quality characterization models generated based on different types of data collected in Blocks S110-S140 and predicting a final sleep quality value based on the different values, such as by averaging the different values; etc.). Applying a plurality of sleep characterization models suited to different contexts can confer improvements to the processing system by improving sleep characterization accuracy (e.g., by tailoring analysis to a particular user's demographic, behaviors, etc.), retrieval speed for the appropriate sleep characterization model from a database (e.g., by associating customized sleep characterization models with particular user accounts and/or other identifiers), training and/or execution of sleep characterization models (e.g., where the customized sleep characterization models are associated with a subset of a pool of potential sleep-related features correlated with sleep-related parameters and/or conditions, and where the remaining unselected features are less correlated), and/or other suitable aspects of the processing system. However, applying any number of sleep characterization models can be performed in any suitable manner.

Figure 3B:
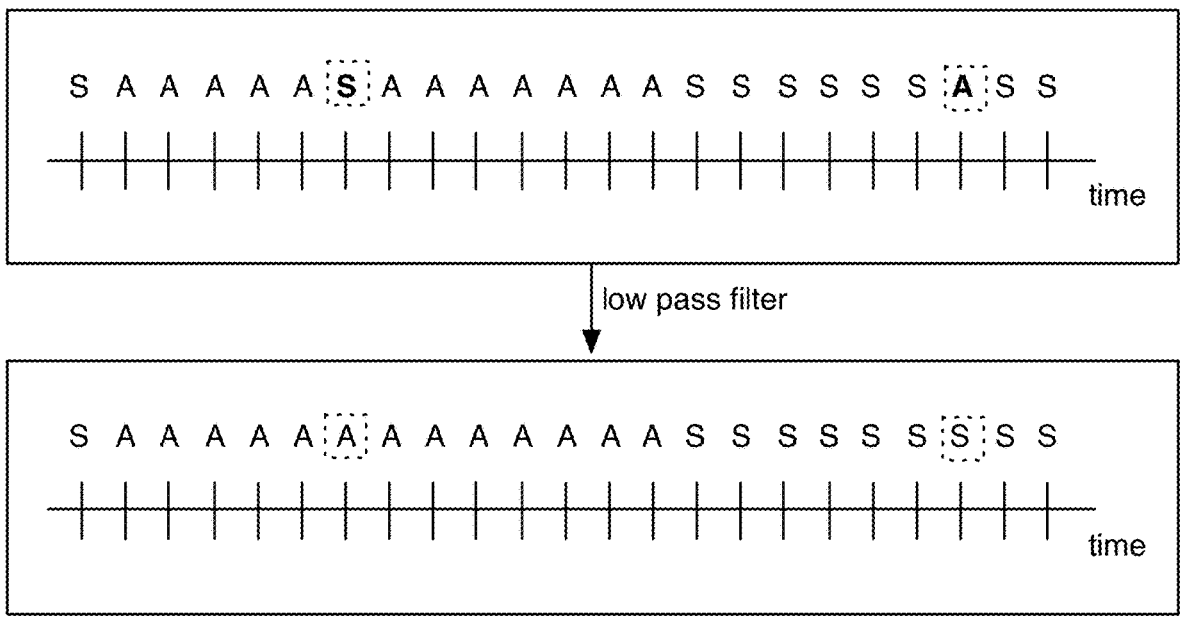

An output of Block S150 can include a sleep dataset, where the sleep dataset includes a set of time points, each tagged as one of an awake time point (e.g., with an associated confidence value) and an asleep time point (e.g., with an associated confidence value). The sleep dataset can further be used to determine one or more derivative sleep-related parameters including: a start time and an end time of each of a set of sleeping periods, a start time and an end time of each of a set of awake periods, bedtimes, waking times, sleep quality (e.g., in terms of restful vs. restless sleep), and any other suitable sleep-related parameters of the user. Furthermore, while the sleep dataset can have a binary state (e.g., asleep, awake) associated with each time point, alternative variations of the sleep dataset can additionally or alternatively include a non-binary state (e.g., sleep restfulness along a spectrum, etc.) associated with one or more time points of the set of time points. In variations, Block S150 and/or other portions of the method 100 can additionally or alternatively include processing the sleep dataset and/or any other suitable datasets with one or more operations configured to adjust extraneous data points, erroneous data point, and/or data points associated with low confidence values. In variations, the operation(s) can include one or more of: a filtering operation, a smoothing operation, a windowing operation, a clipping operation, an extrapolation operation, and/or any other suitable operation. For instance, in one example as shown in FIG. 3B, a low pass filter can be applied to the sleep dataset. In more detail, the low pass filter can thus remove data points having a high probability of being erroneous (e.g., an awake time point surrounded by asleep data points, an asleep time point surrounded by awake data points, etc.) from the sleep dataset. Additionally or alternatively, Block S150 can include implementation of machine learning techniques to develop models for detection of asleep times and/or awake times. Such techniques can include implementation of one or more of: classification approaches to predict asleep/awake states, clustering approaches to detect related time periods associated with asleep/awake states, association rule mining approaches, and/or any other suitable technique. Any other suitable operation(s) can, however, be applied to the sleep dataset.

In variations, Block S150 can additionally or alternatively include validating one or more data points of the sleep dataset against other data provided by outputs of one or more of Block S110-S140. For instance, data points of the sleep dataset can be validated against self-assessed sleep data from the survey dataset, in order to validate or correct one or more data points of the sleep dataset. Validation of data points of the sleep dataset can, however, be performed using any other suitable data. In variations, Block S150 can additionally or alternatively include one or more of: identifying sleep patterns of the user; detecting deviations from identified sleep patterns of the user; generating an alert upon detection of an adverse deviation from an identified sleep pattern of the user; generating an alert upon detection of a positive deviation from an identified sleep pattern of the user; identifying correlations between sleep behaviors of the user and other behaviors of the user extracted from one or more of the log of use, the supplementary dataset, the device event dataset, and the survey dataset; anticipating sleep behavior of the user at a future time point, based upon processing data from the user with a predictive model; and performing any other suitable analysis or activity.

Regarding Block S150, generating one or more of: the predictive analysis to anticipate future states of the user, the correlational analyses to identify correlations between sleep behaviors and sleep-related conditions of the user, comparative analyses between different components of the dataset of Blocks S110-S140 and threshold conditions, the analyses associated with identifying sleep patterns of the user, and the alerts configured to trigger appropriate interventions for the user can be performed in a manner analogous to embodiments, variations, and examples of the methods described in in U.S. application Ser. No. 14/839,053 entitled "Method for Modeling Behavior and Depression State" and filed on 28 Aug. 2015 and U.S. application Ser. No. 14/839,232 entitled "Method for Modeling Behavior and Psychotic Disorders" and filed on 28 Aug. 2015. However, characterizing sleep-related parameters S150 can be performed in any suitable manner.

3.6 Method—Determining a Sleep Care Plan

Block S160 recites: determining a sleep care plan for the user based on one or more sleep-related parameters, the sleep care plan including a therapeutic intervention. Block S160 functions to determine one or more therapeutic interventions for one or more users, where the therapeutic interventions are configured to improve a sleep-related parameter, a sleep-related condition, the user's sleep behavior, overall health, and/or other suitable aspects. Block S160 can additionally or alternatively include determining (and/or promoting as in Block S170) therapeutic interventions for the user based upon one or more of: a detection of a deviation from a sleep pattern of the user; an anticipated future sleep-related condition (e.g., poor sleep episode) of the user based upon an identified correlation with one or more other behaviors/events of the user; an anticipated effect of past, current, or future sleep behavior on a comorbid disorder; an anticipated effect of a state of a comorbid disorder on past, current, or future sleep behavior of the user; and/or any other suitable factor conducive to determination and/or provision of an intervention.

Regarding Block S160 therapeutic interventions can include any one or more of: sleep-related notifications; therapy interventions (e.g., cognitive behavioral therapy exercises; etc.); care provider-related interventions (e.g., telemedicine, as shown in FIG. 7; scheduling care provider appointments; etc.); physical interventions (e.g., breathing exercises; meditation exercises; acupuncture; hypnosis; brain stimulation such as through magnetic pulses and/or electrical stimulation; etc.); dietary interventions; medication interventions; auditory interventions (e.g., controlling the mobile communication device to emit music samples in accordance with music therapy; etc.); mobile device and/or supplementary sleep-related device interventions (e.g., modifying device operation parameters; etc.); ambient environment interventions (e.g., modification of light parameters, air quality and/or composition parameters, temperature parameters, humidity parameters; etc.) and/or any other suitable types of treatments. For example, the method 100 can include determining a telemedicine intervention; automatically facilitating, through a wireless communicable link, a digital telemedicine communication between the mobile device associated with the user and a care provider mobile device associated with a care provider; and determining an updated therapeutic intervention based on the digital telemedicine communication, a second log of use dataset (e.g., collected after promotion of the original therapeutic intervention), and a therapeutic intervention model. In another example, Blocks S160-S170 can include: determining a therapeutic intervention including a modification to a display brightness of a mobile device (e.g., where the modification is operable to improve the display of the mobile device); and promoting the modification to the display brightness at the mobile device to improve a sleep-related condition.

Figure 5:
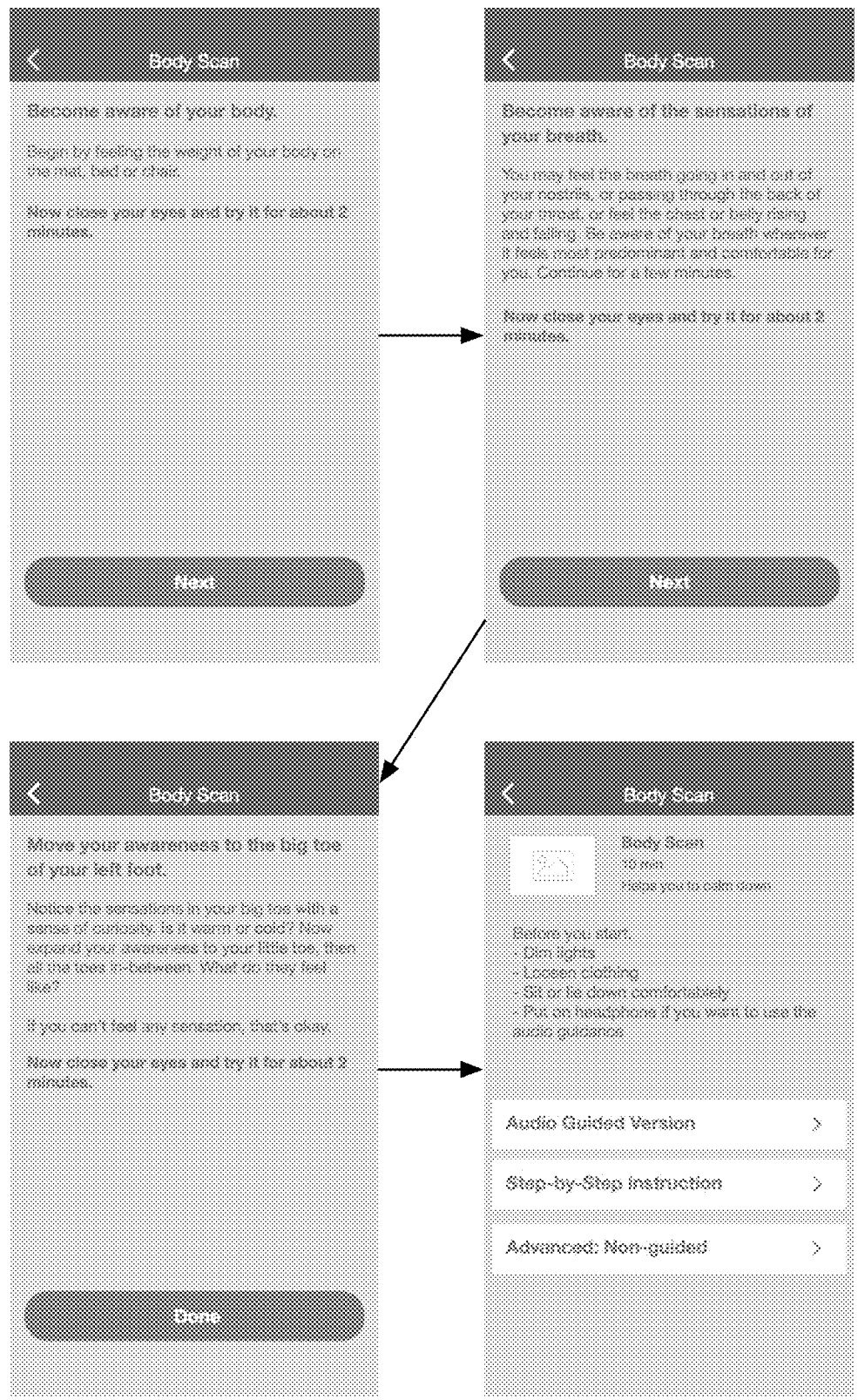
FIG. 5 depicts an example of a relaxation intervention.
Figure 6A:
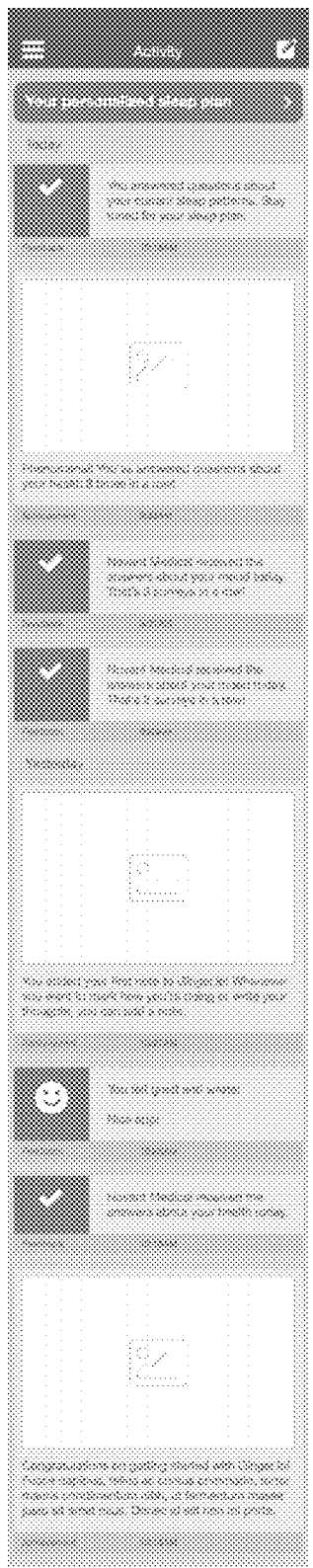
FIGS. 6A-6E depict example interventions.
Figure 6B:
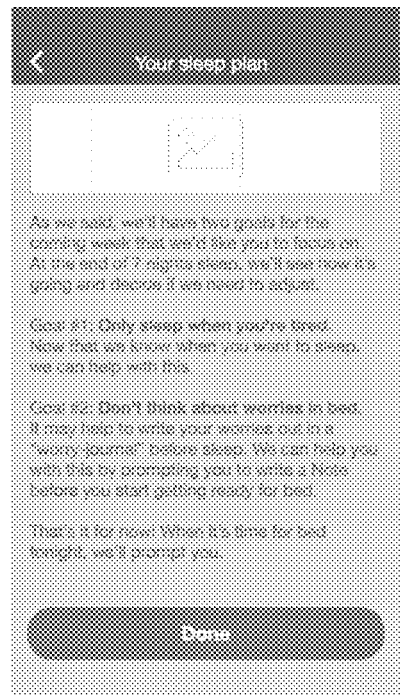
Figure 6C:
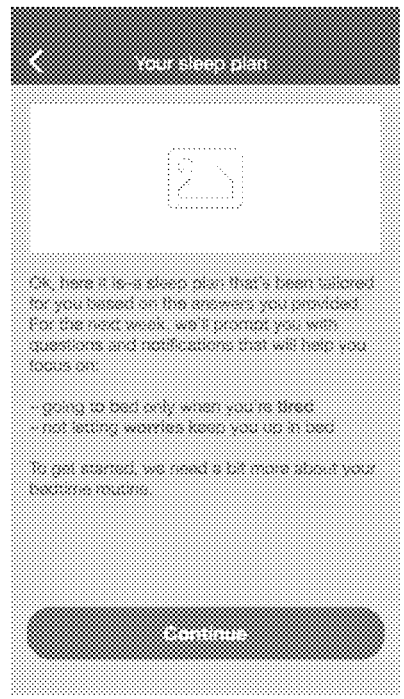
Figure 6D:
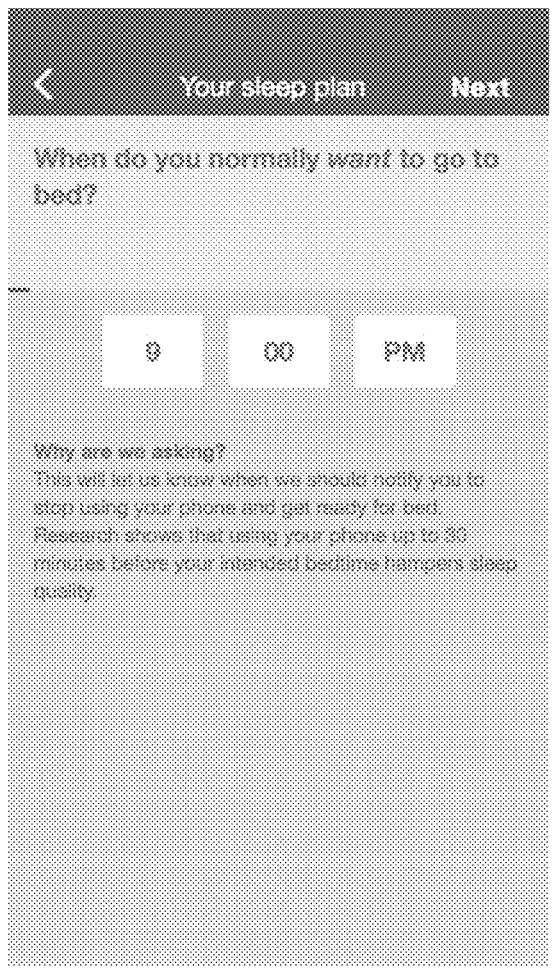
Figure 6E:
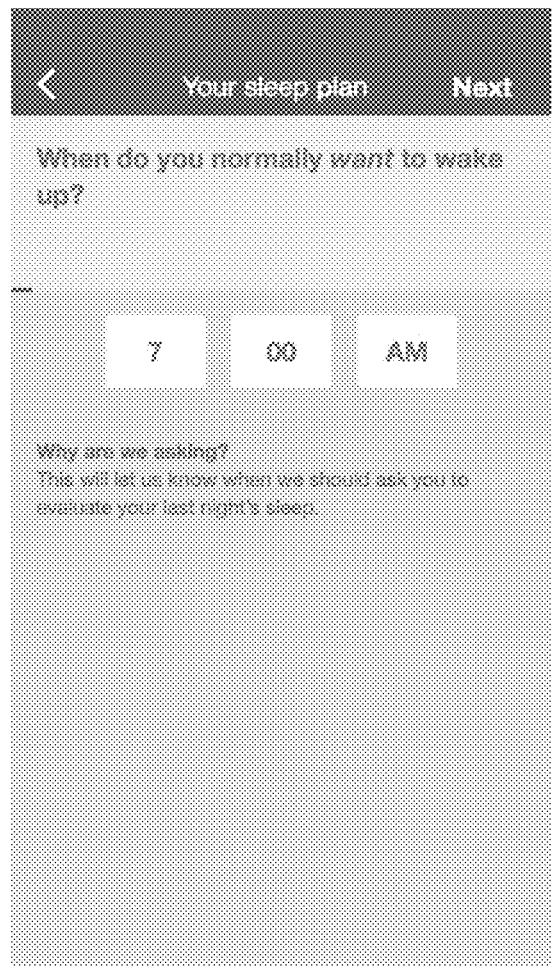

In Block S160, the therapeutic intervention(s) can be in any one or more forms including: visual (e.g., text-based or graphic intervention rendered within an application executing at the mobile communication device), numerical (e.g., including sleep-related parameters in an educational notification; etc.), audio (e.g., using a speaker module of the mobile device), haptic (e.g., using a vibration motor of the mobile device), and/or any other suitable form. In one example, a mobile communication device of a user can download (e.g., upon initiation of download by one or more of the user and an entity associated with the user; based on a hyperlink; etc.) and subsequently render portions of an intervention for the user at a display of the mobile communication device. The intervention(s) can be personalized to the user, or can be provided in the same manner to each of a population of users. In one example, Block S160 can include providing a relaxation intervention that allows the user to become more aware of his/her body, as shown in FIG. 5. In the relaxation intervention, the user can be guided (e.g., visually, audibly), or unguided in becoming aware of his/her body in phases, which can help the user to relax and make falling asleep easier. In another example, as shown in FIGS. 6A-6E, the selected intervention can provide the user with a summary of his/her progress in managing sleep behavior, and provide the user with a personalized sleep care plan according to the user's desired sleep goals (e.g., wakeup times, bedtimes, etc.).

In a variation of Block S160, therapeutic interventions can include one or more sleep-related notifications (e.g., which can be presented at the mobile communication device for which a log of use was collected in Block S110). The sleep-related notifications can include educational content (e.g., a list of benefits from healthy sleep behaviors; etc.); sleep-related parameters (e.g., characterized in Block S150); information on associated sleep-related conditions; recommendations and/or suggestions; hyperlinks (e.g., URLs, URIs, etc.) to sleep-related content, and/or any other suitable content. In examples, Block S160 can include modifying the visually perceptible elements of the sleep-related notification, such as one or more of the: font, brightness, color, associated graphics, and/or other suitable visually perceptible elements, but any suitable perceptible elements (e.g., auditory elements) can be modified. Modifying perceptible elements can provide a technological approach to improving the display of the device at which the sleep-related notification is presented (e.g., selecting brighter colors for the sleep-related notification during daytime to improve user engagement with the therapeutic intervention; selecting darker colors during nighttime to minimize brain stimulation and associated sleep latency; etc.). In an example, Block S160 can include: generating a sleep-related notification based on the sleep-related parameter, the log of use dataset, the motion supplementary dataset, and a hyperlink to sleep-related content; and modifying a visually perceptible digital element associated with the sleep-related content to improve display of the sleep-related notification for improving the sleeping-related disorder. However, generating sleep-related notifications can be performed in any suitable manner.

In variations of Block S160 therapeutic interventions can include temporally associated therapeutic interventions including one or more of: pre-sleeping period therapeutic interventions, during-sleeping period therapeutic interventions, and/or post-sleeping period therapeutic interventions (e.g., where a treatment system is operable to automatically initiate provision of pre-sleeping period treatments prior to the sleeping period, and operable to automatically initiate provision of post-sleeping period treatments after the sleeping period). Determining temporally associated therapeutic interventions can additionally or alternatively be based on other temporally associated therapeutic interventions and/or associated evaluations of improvement. For example, the method 100 can include: receiving a log of use dataset, a motion supplementary dataset, and/or any other suitable data during a sleeping period, such as in real-time during a sleeping period associated with the promotion of a pre-sleeping period therapeutic intervention; and determining a post-sleeping period treatment based on the pre-sleeping period treatment, a sleep-related parameter (e.g., characterized in relation to the sleeping period), the log of use dataset, the motion supplementary dataset, and/or any other suitable data. However, temporally associated therapeutic interventions can be configured in any suitable manner.

Block S160 preferably includes determining (e.g., generating, updating, etc.) one or more sleep care plans for one or more users, where a sleep care plan is preferably operable to improve a sleep-related condition (e.g., sleeping-related disorder), but can additionally or alternatively be operable to improve any suitable aspect. Sleep care plans preferably include one or more therapeutic interventions, one or more therapeutic intervention parameters (e.g., specifying timing, geographical location, frequency, threshold conditions, device data for devices to be controlled by the therapeutic interventions, and/or other suitable aspects of promoting the therapeutic interventions), and/or any other suitable data (e.g., sleep-related parameters, diagnoses, user information, etc.). For example, a sleep care plan can specify promoting a sleep-related notification in response to detection of a user geographical location of their bedroom at nighttime. Determining therapeutic intervention parameters for a sleep care plan can be based on any suitable data described above in relation to determining therapeutic interventions. For example, the method 100 can include: determining (e.g., updating) a target geographical location for promoting a therapeutic intervention to the user based on a log of use dataset and a motion supplementary dataset (e.g., emitting a warning auditory message in response to detecting a user entering a living room during a sleep session, based on historic digital communication patterns of the user awakening during a sleep session to make phone calls in the living room); determining a user location based on a current motion supplementary dataset corresponding to a motion-related sensor of the mobile device; and in response to the user location matching the updated target geographical location (e.g., living room), promoting the updated therapeutic intervention to the user according to the sleep care plan. Sleep care plans are preferably personalized to a user (e.g., based on sleep-related parameters characterized for the user; based on the user's digital communication behaviors, mobility behaviors; etc.), but can alternatively be user-agnostic. However, sleep care plans can be configured in any manner analogous to dynamic care plans described in performed in any manner analogous to U.S. application Ser. No. 15/265,454 entitled "Method for Providing Health Therapeutic Interventions to a User" and filed on 14 Sep. 2016, which is herein incorporated in its entirety by this reference, and/or in any suitable manner.

Regarding Block S160 determining a sleep care plan (e.g., a therapeutic intervention of a sleep care plan) is preferably based on a sleep-related parameter. For example, Block S160 can include mapping a sleep-related parameter value (e.g., falling within a range; satisfying a threshold condition; of a certain type and magnitude; etc.) to one or more therapeutic intervention types associated with the sleep quality parameter value. In another example, Block S160 can include: determining breathing exercises for a sleep care plan based on a breathing parameter value falling below a threshold. In another example, Block S160 can include: by way of the mobile communication device, determining an intervention to the user upon detection that the user has experienced a poor sleep episode, based upon an analysis of a set of sleep-related parameters. In variations, determining a sleep care plan can be based on at least one of a log of use dataset, supplementary dataset, device event dataset, survey dataset, and/or any other suitable data. For example, the method 100 can include: identifying a correlation between poor sleep quality (e.g., based on post-sleep session survey datasets) and late-night phone calls in the bedroom (e.g., based on digital communication-mobility behavior features); and determining a therapeutic intervention (e.g., promoting a sleep-related notification in response to detecting activation of a native phone calling application in the bedroom during nighttime, based on device event data and motion supplementary data). However, determining sleep care plans can be based on any suitable data.

Determining a sleep care plan in Block S160 can additionally or alternatively include determining and/or applying sleeping-related features (e.g., analogous to Block S150). For example, Block S160 can include: extracting a set of sleeping-related features (e.g., from a log of use dataset) including at least one of a phone call duration and a phone call frequency, and determining a therapeutic intervention (and/or other aspects of a sleep care plan) based on a therapeutic intervention model and the at least one of the phone call duration and the phone call frequency. Leveraging sleeping-related features in Block S160 can include applying the same or different computer-implemented rules (e.g., operable to improve accuracy of determining sleep care plans, such as with a therapeutic intervention model for personalizing sleep care plans to different users; etc.) described in relation to Block S150. For example, the same digital communication-mobility feature extracted based on a feature engineering computer-implemented rule, a log of use dataset, and a motion supplementary dataset can be used in both characterizing a sleep-related parameter and determining a sleep care plan. Additionally or alternatively, the method 100 can include: characterizing a sleep-related parameter based on a first feature extracted from a dataset (e.g., a text messaging feature extracted from a log of use dataset according to a first feature engineering rule); and determining a therapeutic intervention based on a second feature (and/or the sleep-related parameter) extracted from the same dataset (e.g., a phone calling feature extracted from the log of use dataset according to a second feature engineering rule). However, determining sleep care plans based on sleeping-related features can be performed in any suitable manner.

In relation to Block S160 determining a sleep care plan can include generating and/or applying a therapeutic intervention model, which can be performed in any manner analogous to approaches described in relation to sleep characterization models (e.g., in Block S150; different sleep characterization models for different purposes; machine learning therapeutic intervention models; etc.). Therapeutic intervention models preferably output types of therapeutic interventions (and/or therapeutic intervention parameters) based on inputs extracted from sleep-related parameters, sleep-related features, and/or other suitable data (e.g., datasets from Blocks S110-S140), where the outputs are preferably personalized to the user. For example, the method 100 can include: identifying a correlation between decreased sleep latency and presentation of a sleep-related recommendation (e.g., advising against excessive blue light exposure from mobile devices) 30 minutes prior to a sleep session, for a subgroup of users with a sleep latency above a threshold; generating a therapeutic intervention model based the correlation; and in response to characterizing a sleep latency above the threshold for a current user, determining a sleep care plan including a scheduled presentation of the sleep-related recommendation, based on the therapeutic intervention model. In another example, Block S160 can include training a machine learning therapeutic intervention model with a set of training samples, each training sample including sleeping-related features and a label of a therapeutic intervention type correlated with improvement in a sleep-related condition associated with the sleeping-related features. However, therapeutic intervention models can additionally or alternatively output any suitable aspect of a sleep care plan, and/or any suitable information. Generating therapeutic intervention models can include applying the same or different algorithms as generating sleep characterization models. Additionally or alternatively, generating and/or applying therapeutic intervention models can be performed in any suitable manner.

Figure 1A:
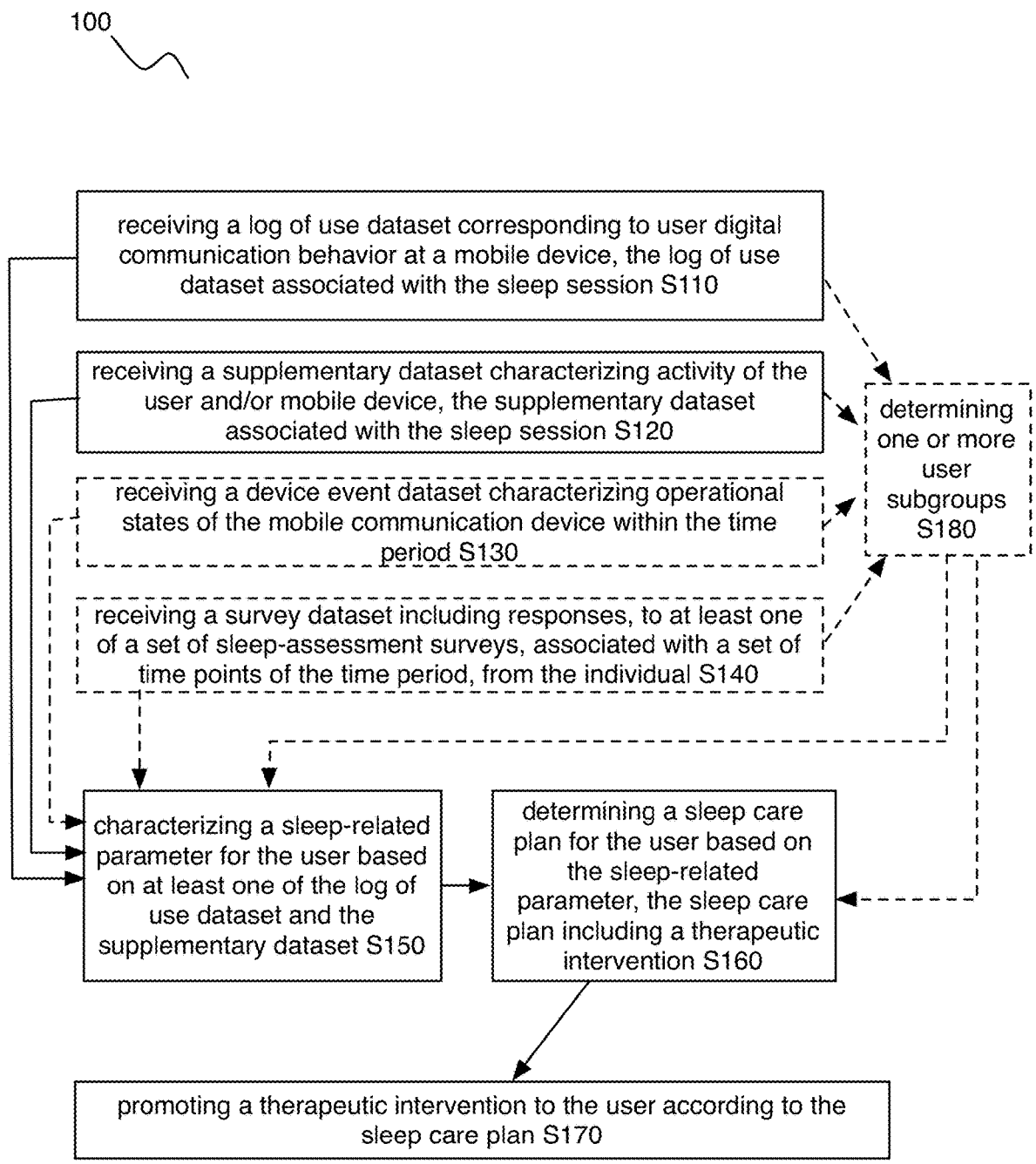
FIGS. 1A-1B are flowcharts of variations of a method.
Figure 1B:
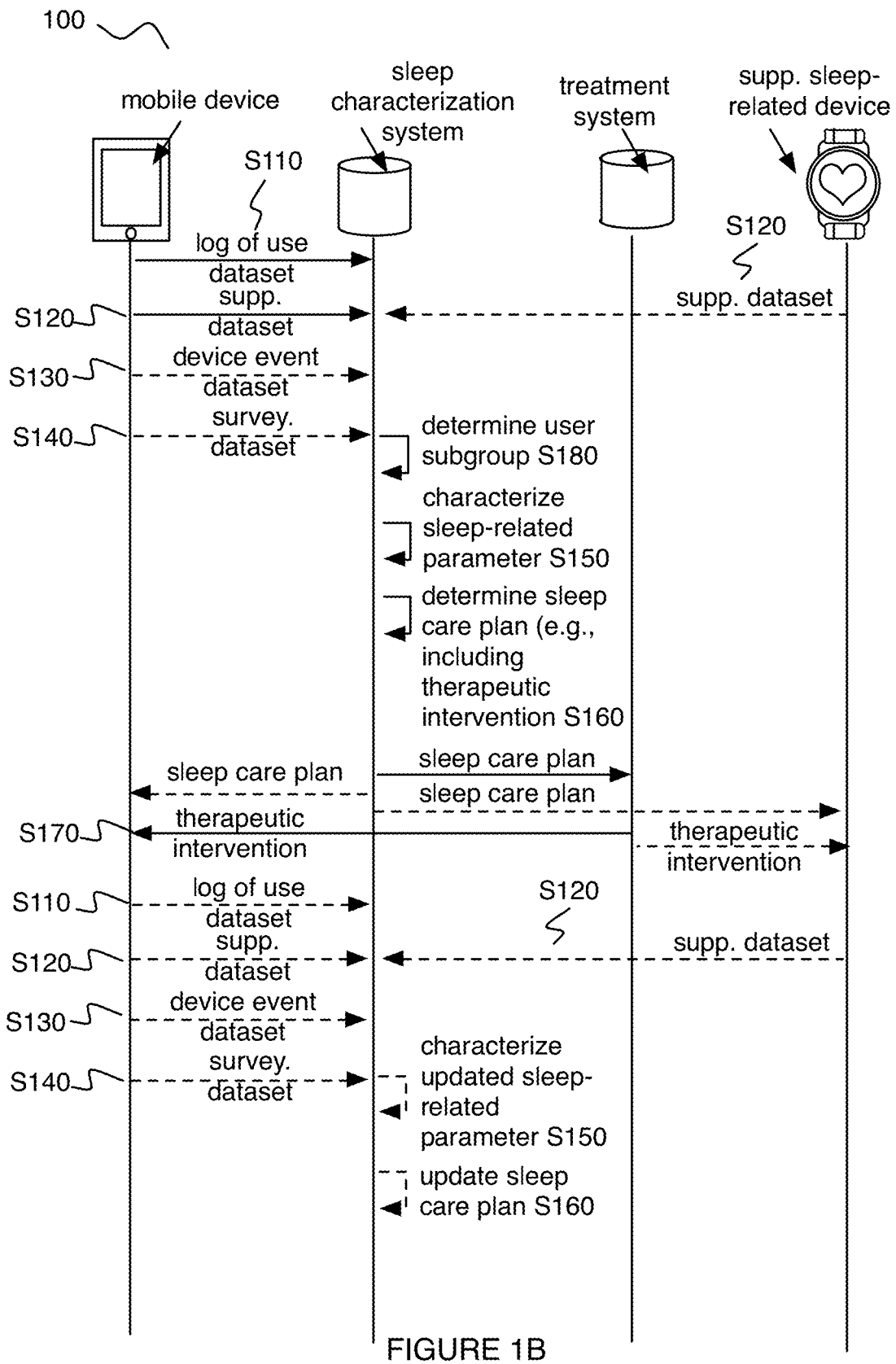
Figure 4:
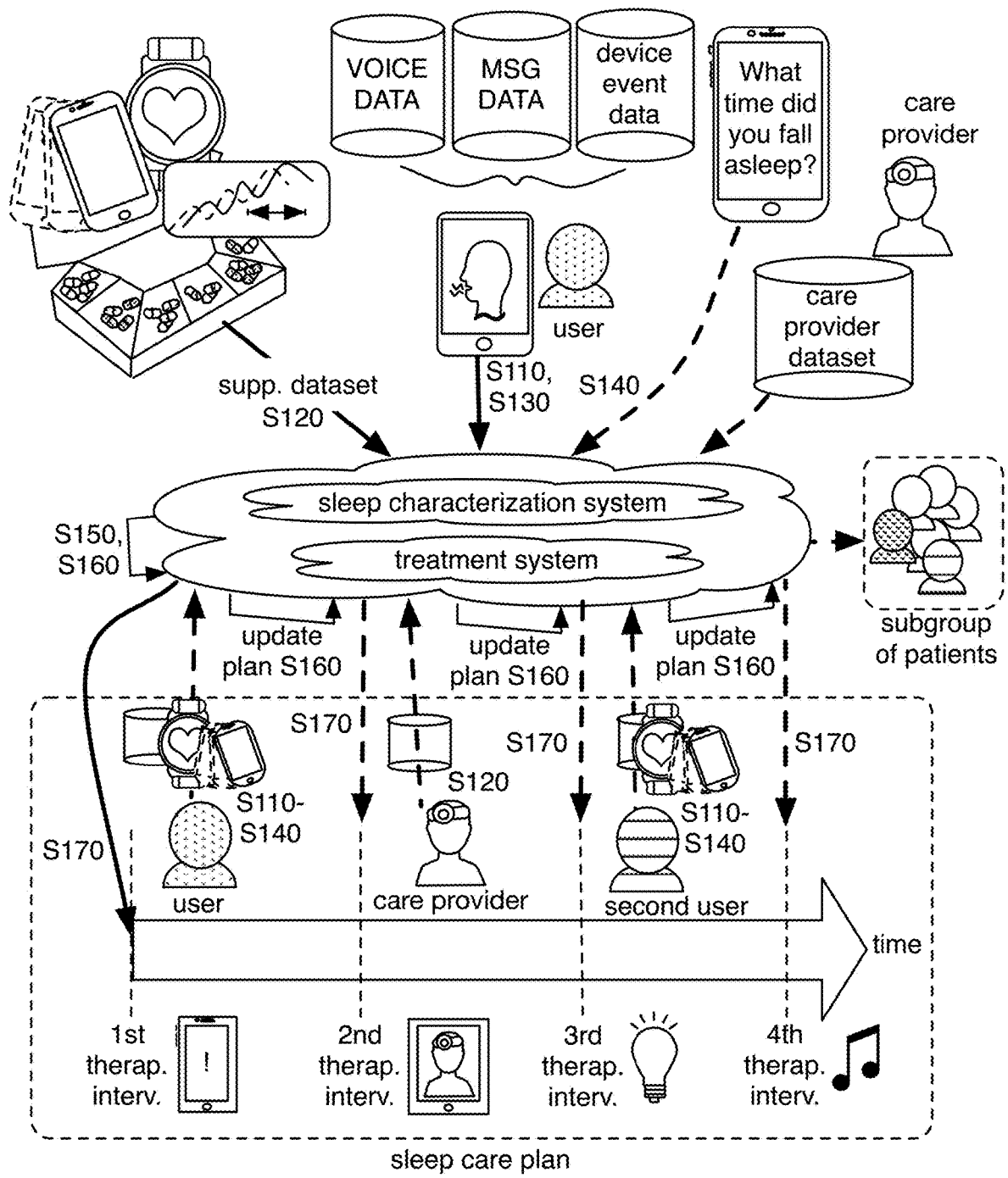
FIG. 4 illustrates a schematic representation of variations of a method.

As shown in FIGS. 1B and 4, in variations of Block S160, determining sleep care plans can include dynamically updating one or more sleep care plans (e.g., updating therapeutic interventions and/or therapeutic intervention parameters, etc.). Updating a sleep care plan is preferably based on an evaluation of improvement of one or more users to one or more therapeutic interventions (e.g., administered according to a sleep care plan). Evaluations of improvement are preferably determined based on survey datasets (e.g., including post-sleep session survey responses; analyzing survey datasets for statistically significant changes in sleep-related parameters due to therapeutic interventions; etc.), but can additionally or alternatively be based on sleep-related parameters (e.g., changes in characterized sleep-related parameters over time), log of use datasets (e.g., identifying improvements in digital communication behavior associated with sleep sessions, due to real-time sleep-related notifications), motion supplementary datasets (e.g., identifying improvements in amount of physical activity), other datasets described in Blocks S110-S140, and/or any other suitable data. For example, the method 100 can include: promoting a therapeutic intervention in association with a first sleep session, based on a first log of use dataset; and updating the therapeutic intervention based on a second log of use dataset collected in association with the first sleep session, where a sleep care plan includes a schedule for promotion of the updated therapeutic intervention for a second sleep session. In another example, evaluations of improvements for other users can be used in updating sleep care plans for a current user. In a specific example, the method 100 can include: promoting a therapeutic intervention in association with a sleep session of a second user; receiving a digital response from the second user to a digital survey associated with the sleep session; generating an evaluation of improvement in the second user to the therapeutic intervention based on the digital response; and determining an updated therapeutic intervention for a sleep care plan for a first user based on a log of use dataset (e.g., collected after provision of the original therapeutic intervention to the first user) and the evaluation of improvement in the second user (and/or a therapeutic intervention model). Additionally or alternatively, updating sleep care plans can be performed in any suitable manner. However, determining therapeutic interventions (and/or promoting therapeutic interventions in Block S170) can be performed in any manner analogous to that described in U.S. application Ser. No. 15/265,454 entitled "Method for Providing Health Therapeutic Interventions to a User" and filed on 14 Sep. 2016, and U.S. application Ser. No. 15/245,571 entitled "Method and System for Modeling Behavior and Heart Disease State" and filed on 24 Aug. 2016, each of which are herein incorporated in their entirety by this reference, and/or in any suitable manner.

3.7 Method—Promoting a Therapeutic Intervention

Block S170 recites: promoting a therapeutic intervention to the user according to the sleep care plan (e.g., therapeutic intervention parameters included in the sleep care plan). Block S170 functions to automatically and actively promote improvements to the user's sleep behavior, and/or to facilitate maintenance of a healthy state in the user. Promoting therapeutic interventions can include: generating control instructions (e.g., for operating one or more mobile devices and/or supplementary sleep-related devices); communicating with devices (e.g., transmitting control instructions, sleep-related notifications, and/or other suitable data to mobile devices and/or supplementary sleep-related devices; receiving sensor data from such devices; etc.); controlling and/or operating devices; retrieving data (e.g., retrieving sleep-related notification content from databases associated with the sleep characterization system and/or treatment system; etc.); and/or any other suitable operation. In an example, Block S170 can include controlling a temperature control system to adjust a temperature parameter (e.g., associated with a first sleep session), and/or controlling a lighting control system to adjust a lighting parameter (e.g., associated with a second sleep session, where controlling the lighting control system is an updated therapeutic intervention for a sleep care plan). In another example, promoting a therapeutic intervention can include presenting therapeutic intervention recommendations to one or more care providers, where the care providers can subsequently provide the therapeutic intervention (and/or a modified therapeutic intervention) to the user.

Block S170 can be based on any suitable data described in relation to Block S160 and/or other suitable Blocks of the method 100. For example, Block S160 and/or S170 can be performed according to an assessment of criticality of the condition of the user in relation to sleep behavior. The intervention(s) provided to the user in Block S170 can additionally or alternatively be provided according to an assessment of appropriateness to a state of the user. For instance, in some variations, Block S170 can include determining how receptive the user would be to an intervention (e.g., based upon identification of a location of the user, based upon identification of an activity being performed by the user, based upon identification of a cognitive state of the user, etc.) and can, in some variations, include delaying provision of an intervention to the user until a future time when the user is more likely to be receptive to the intervention. Interventions can, however, be provided to the user at any other suitable time(s) in Block S170. In another variation, Block S170 can include promoting a therapeutic interventions based on a ranking of devices (e.g., mobile devices, supplementary sleep-related devices) at which to promote the therapeutic intervention. For example, Block S170 can include automatically promoting a therapeutic intervention at a secondary treatment system in response to failing to establish a wireless communicable link with the mobile device, where the secondary treatment system includes a supplementary sleep-related device.

Regarding Block S170, in relation to any alerts generated, alerts can be used to trigger the interventions provided in Block S170. For instance, the method 100 can thus include generating an alert upon detection, at the sleep characterization system performing the analyses associated with the method 100, that the user is deviating from a sleep pattern in an adverse manner, or that the user is anticipated to have an episode of poor sleep, based upon analysis of a set of activities performed by the user. The alert(s) can thus include an alert that prompts transmission of a notification to an entity associated with the user, for instance, for therapeutic intervention. The alert(s) can additionally or alternatively include an alert that serves as an input into a subsequent computer-implemented module for automatically providing an intervention to the user, the intervention intended to improve the sleep-related state of the user. Alerts can, however, be used to drive interventions in any other suitable manner.

In some variations, as shown in FIG. 4, Block S170 can include automatically initiating provision of the intervention for the user by way of at least one of the sleep characterization system and the mobile device. Furthermore, the interventions can be provided using one or more of: healthcare provider interactions, pharmaceutical compound distributors (e.g., sleep aid distributors, where the user can receive prescription and/or over-the-counter sleep aids), homeopathic sleep treatment centers, mobile application implemented methods, web browser-facilitated methods, and any other suitable avenue of therapy provision. The intervention(s) can additionally or alternatively be provided in a manner similar to that described in U.S. application Ser. No. 13/969,339, entitled "Method for Modeling Behavior and Health Changes" and filed on 16 Aug. 2013, with therapy/treatment efficacy analyzed by a treatment regimen model and/or a treatment efficacy model. However, Blocks S160 and S170 can be performed in any analogous fashion, and promoting therapeutic interventions can be performed in any suitable manner.

3.8 Method—Determining a User Subgroup

The method 100 can additionally or alternatively include Block S180, which recites: determining one or more user subgroups. Block S180 functions to group one or more users based on shared characteristics (e.g., similar sleep-related behaviors, digital communication behaviors, sleep-related parameters, and/or any other suitable data), in order to facilitate performing Blocks S160-S170 and/or other suitable portions of the method 100 in association with user subgroups. For example, the method 100 can include: assigning the user to a sleep-related subgroup of a set of sleep-related subgroups, based on sleep survey data (and/or a log of use dataset, a motion supplementary dataset, and/or other suitable data) collected from the user, where the sleep-related subgroup shares a sleeping-related characteristic; and processing the set of sleeping-related features with a sleep characterization model tailored to the sleep-related subgroup to improve accuracy of the sleep characterization. However, determining and/or leveraging user subgroups can be performed in any suitable manner analogous to U.S. application Ser. No. 13/969,339, entitled "Method for Modeling Behavior and Health Changes" and filed on 16 Aug. 2013, and/or in any suitable manner.

The method 100, however, can include any other suitable Blocks and/or steps configured to model behavior and/or improve sleep-related conditions associated with a user.

4. System

Figure 2:
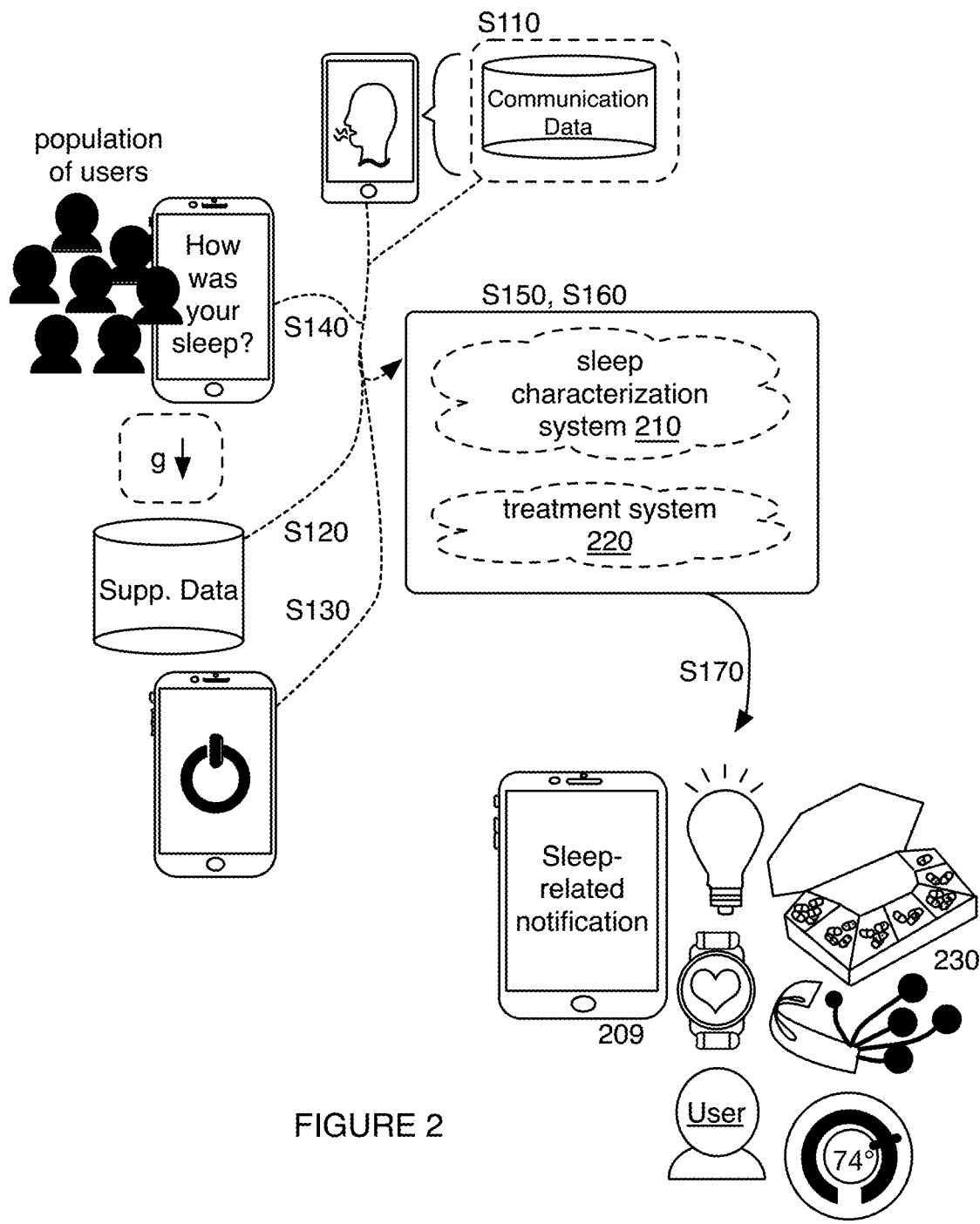
FIG. 2 is a schematic of variations of a method and system.

As shown in FIG. 2, an embodiment of a system 200 for characterizing and/or treating a sleep-related condition for a user associated with a sleep session (e.g., sleeping period) includes: a sleep characterization system 210 operable to receive a log of use dataset corresponding to user digital communication at a mobile device 209, the log of use dataset associated with the sleep session, receive a motion supplementary dataset corresponding to a motion-related sensor of the mobile device 209, the motion supplementary dataset associated with the sleep session, characterize a sleep-related parameter for the user based on the log of use dataset and the motion supplementary dataset, and determine a treatment for the sleeping-related disorder based on the sleep-related parameter, the log of use dataset, and the motion supplementary dataset; and a treatment system 220 operable to automatically initiate provision of the treatment to the user. The sleep characterization system 210 and/or treatment system 220 can include a processing system 205, an interface 207 with a communication data aggregation module executing on a mobile communication device 209 of the user; and/or any other suitable modules operable to perform any suitable portions of the method 100. The system 200 can additionally or alternatively include a supplemental sleep-related device 230 and/or any other suitable components. However, the system 200 and associated components can be configured in any manner analogous to U.S. application Ser. No. 13/969,339 entitled "Method for Modeling Behavior and Health Changes" and filed on 16 Aug. 2013, U.S. application Ser. No. 15/265,454 entitled "Method for Providing Health Therapeutic Interventions to a User" and filed on 14 Sep. 2016, and U.S. application Ser. No. 15/245,571 entitled "Method and System for Modeling Behavior and Heart Disease State" and filed on 24 Aug. 2016, each of which are herein incorporated in their entirety by this reference, and/or configured in any suitable manner.

The sleep characterization system 210 functions to collect and process datasets (e.g., described in Blocks S110-S140) in characterizing sleep-related parameters and/or determining therapeutic interventions. The sleep characterization system 210 is preferably adherent to health-related privacy laws (e.g., HIPAA), and is preferably configured to privatize and/or anonymize data according to encryption protocols. In an example, when a user installs and/or authorizes collection and transmission of personal communication data by the system 200 through the native data collection application, the application can prompt the user to create a profile or account. In the example, the account can be stored locally on the user's mobile communication device 209 and/or remotely. For example, private health-related data can be stored temporarily on the user's mobile communication device in a locked and encrypted file folder on integrated or removable memory. In this example, the user's data can be encrypted and uploaded to the remote database once a secure Internet connection is established. However, data can be stored and/or transmitted in any suitable manner.

The treatment system 220 functions to promote one or more therapeutic interventions according to one or more sleep care plans. Additionally or alternatively, the sleep characterization system 210 can include the treatment system, and can include functionality associated with promoting therapeutic interventions. The treatment system 220 can include any one or more of supplementary sleep-related devices 230 (e.g., ambient environment devices such as sensing and control systems for temperature, light, air quality and/or composition, humidity; biometric devices such as cardiovascular, EEG, EOG, EMG, ECG; medication devices such as automatic medication dispensers; etc.), mobile devices 209 (e.g., mobile communication devices from which a log of use dataset is collected; user devices; care provider devices;), and/or any other suitable devices, but any of the devices can be independent from the treatment system 220. In an example, a remote sleep characterization system 210 can be operable to generate a sleep-related notification, and the treatment system 220 can be operable to transmit the sleep-related notification to the target mobile device 209. However, the treatment system and/or supplementary sleep-related devices 230 can be configured in any suitable manner.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a computer or mobile device 209, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions. The embodiments include every combination and permutation of the various system components and the various method processes, including any variations, examples, and specific examples.

As a person skilled in the art will recognize from the previous detailed description and from the figures and claims, modifications and changes can be made to the embodiments of the invention without departing from the scope of this invention as defined in the following claims.

We claim:

1. A system for treating a sleeping-related disorder for a user associated with a sleeping event, the system comprising:
   a sleep characterization system operable to:
   receive a log of use dataset corresponding to user digital communication at a mobile device, the log of use dataset associated with the sleeping event;
   receive a motion supplementary dataset corresponding to a motion-related sensor of the mobile device, the motion supplementary dataset associated with the sleeping event;
   characterize a sleeping parameter for the user based on the log of use dataset and the motion supplementary dataset;
   assign the user to a sleep-related subgroup of a set of sleep-related subgroups based on the sleeping parameter;
   determine a treatment for the sleeping-related disorder based on the sleeping parameter, the log of use dataset, the motion supplementary dataset and a therapeutic intervention model, wherein the therapeutic intervention model is determined based on the sleep-related subgroup; and
   a treatment system operable to automatically initiate provision of the treatment to the user, wherein the treatment comprises a post-sleeping event treatment, wherein the sleep characterization system is further operable to determine a pre-sleeping event treatment for the sleeping-related disorder, and wherein the treatment system is further operable to:
   automatically initiate provision of the pre-sleeping event treatment prior to the sleeping event; and
   automatically initiate provision of the post-sleeping event treatment after the sleeping event.

2. The system of claim 1, further comprising a supplementary sleep-related device comprising a sensor operable to collect sleep-related sensor data associated with the sleeping event, wherein the sleep characterization system is further operable to:
   characterize the sleeping parameter based on the sleep-related sensor data, the log of use dataset, and the motion supplementary dataset; and
   determine the treatment based on the sleep-related sensor data, the sleeping parameter, the log of use dataset, and the motion supplementary dataset.

3. The system of claim 2, wherein the treatment system comprises the supplementary sleep-related device, and wherein the supplementary sleep-related device is operable to promote the treatment to the user.

4. The system of claim 1, wherein the treatment comprises a sleep-related notification, wherein the sleep characterization system is further operable to:
   generate the sleep-related notification based on the sleeping parameter, the log of use dataset, the motion supplementary dataset, and a hyperlink to sleep-related content; and
   modify a visually perceptible digital element associated with the sleep-related content to improve display of the sleep-related notification for improving the sleeping-related disorder.

5. The system of claim 1, wherein the sleep characterization system is further operable to:
   receive the log of use dataset and the motion supplementary dataset during the sleeping event; and
   determine the post-sleeping event treatment based on the pre-sleeping event treatment, the sleeping parameter, the log of use dataset, and the motion supplementary dataset.

6. A method for improving a sleeping-related disorder for a first user, the method comprising
   receiving a first log of use dataset corresponding to user digital communication behavior at a mobile device associated with the first user;
   extracting a set of sleeping-related features from the first log of use dataset based on a feature engineering computer-implemented rule operable to improve accuracy of a therapeutic intervention model;
   assigning the user to a sleep-related subgroup of a set of sleep-related subgroups, wherein the therapeutic intervention model is determined based on the sleep-related subgroup;
   determining a therapeutic intervention for a sleep care plan for the first user based on the set of sleeping-related features and the therapeutic intervention model, the sleep care plan operable to improve the sleeping-related disorder;
   automatically initiating, in association with a first sleep session of the first user, provision of the therapeutic intervention according to the sleep care plan;
   receiving a second log of use dataset corresponding to the user digital communication behavior, the second log of use dataset associated with the first sleep session; and
   determining an updated therapeutic intervention for the sleep care plan based on the second log of use dataset and the therapeutic intervention model, wherein the updated therapeutic intervention is distinct from the therapeutic intervention.

7. The method of claim 6, further comprising:
   wherein promoting the therapeutic intervention comprises automatically facilitating, through a wireless communicable link, a digital telemedicine communication between the mobile device associated with the first user and a care provider mobile device associated with a care provider, and
   wherein determining the updated therapeutic intervention comprises determining the updated therapeutic intervention based on the digital telemedicine communication, the second log of use dataset, and the therapeutic intervention model.

8. The method of claim 6, wherein the sleep care plan comprises a target geographical location for promoting the therapeutic intervention to the first user, wherein determining an updated therapeutic intervention comprises determining an updated target geographical location for the sleep care plan based on the second log of use dataset, and the method further comprising:
   determining a user location based on a motion supplementary dataset corresponding to a motion-related sensor of the mobile device; and
   in response to the user location matching the updated target geographical location, promoting the updated therapeutic intervention to the first user according to the sleep care plan.

9. The method of claim 6, wherein the therapeutic intervention comprises a modification to a display brightness of the mobile device for improving a display of the mobile device, and wherein promoting the therapeutic intervention comprises promoting the modification to the display brightness at the mobile device to improve the sleeping-related disorder.

10. The method of claim 6, wherein promoting the therapeutic intervention comprises controlling a temperature control system to adjust a temperature parameter associated with the first sleep session, and wherein promoting the updated therapeutic intervention comprises controlling a lighting control system to adjust a lighting parameter associated with a second sleep session of the first user.

11. The method of claim 6, further comprising automatically promoting the updated therapeutic intervention at a secondary treatment system in response to failing to establish a wireless communicable link with the mobile device, wherein the secondary treatment system comprises a supplementary sleep-related device.

12. The method of claim 6, further comprising:
promoting the therapeutic intervention in association with a second sleep session of a second user;
receiving a digital response from the second user to a digital survey associated with the second sleep session; and
generating an evaluation of improvement in the second user to the therapeutic intervention based on the digital response,
wherein determining the updated therapeutic intervention for the sleep care plan for the first user comprises determining the updated therapeutic intervention based on the second log of use dataset, the evaluation of improvement in the second user, and the therapeutic intervention model.

13. The method of claim 6, wherein the set of sleeping-related features comprises at least one of a phone call duration and a phone call frequency, and wherein determining the therapeutic intervention comprises determining the therapeutic intervention based on the therapeutic intervention model and the at least one of the phone call duration and the phone call frequency.

14. A method for improving sleep characterization for a user associated with a sleep session, the method comprising:
receiving a log of use dataset corresponding to user digital communication at a mobile device, the log of use dataset associated with the sleep session;
receiving a motion supplementary dataset corresponding to a motion-related sensor of the mobile device, the motion supplementary dataset associated with the sleep session;
extracting a set of sleeping-related features from the log of use dataset and the motion supplementary dataset, based on a feature engineering computer-implemented rule operable to improve accuracy of the sleep characterization;
assigning the user to a sleep-related subgroup of a set of sleep-related subgroups, based on the set of sleeping-related features;
characterizing a sleep-related parameter for the user based on the set of sleeping-related features, wherein characterizing the sleep-related parameter comprises processing the set of sleeping-related features with a sleep characterization model tailored to the sleep-related subgroup to improve accuracy of the sleep characterization; and
automatically initiating provision of a therapeutic intervention to the user based on the sleep-related parameter.

15. The method of claim 14, wherein the log of use dataset comprises a digital communication log entry recorded during the sleep session, the method further comprising identifying an awake period within the sleep session for the user based on the digital communication log entry, wherein characterizing the sleep-related parameter comprises characterizing the sleep-related parameter based on the on the awake period.

16. The method of claim 15, wherein characterizing the sleep-related parameter and promoting the therapeutic intervention are performed in real-time during the awake period within the sleep session.

17. The method of claim 14:
wherein extracting the set of sleeping-related features comprises extracting a digital communication-mobility behavior feature based on processing a text messaging parameter from the log of use dataset with a location parameter from the motion supplementary dataset, according to the feature engineering computer-implemented rule, and
wherein characterizing the sleep-related parameter comprises characterizing the sleep-related parameter based on the mobility-digital communication behavior feature.

18. The method of claim 14, further comprising:
receiving an initial log of use dataset prior to the sleep session; and
receiving an initial motion supplementary dataset prior to the sleep session,
wherein assigning the user to the sleep-related subgroup comprises assigning the user based on the initial log of use dataset, the initial motion supplementary dataset, and the sleep survey data.

* * * * *